US009732359B2

(12) United States Patent
Peng et al.

(10) Patent No.: US 9,732,359 B2
(45) Date of Patent: Aug. 15, 2017

(54) REPLICATION-COMPETENT ADENOVIRAL VECTORS

(71) Applicants: The United States of America as represented by the Secretary of the Department of Health and Human Services, Washington, DC (US); Istituto Superiore di Sanitá, Rome (IT)

(72) Inventors: Bo Peng, Rockville, MD (US); Rebecca Voltan, Ferrara (IT); Barbara Ensoli, Rome (IT); Marjorie Robert-Guroff, Rockville, MD (US)

(73) Assignees: The United States of America, as represented by the Secretary, Department of Health and Human Services, Rockville, MD (US); Istituto Superiore di Sanita, Rome (IT)

( * ) Notice: Subject to any disclaimer, the term of this patent is extended or adjusted under 35 U.S.C. 154(b) by 61 days.

(21) Appl. No.: 14/963,172

(22) Filed: Dec. 8, 2015

(65) Prior Publication Data
US 2016/0090606 A1 Mar. 31, 2016

Related U.S. Application Data

(62) Division of application No. 14/571,942, filed on Dec. 16, 2014, now Pat. No. 9,216,214, which is a division of application No. 11/282,319, filed on Nov. 17, 2005, now Pat. No. 8,926,987.

(60) Provisional application No. 60/629,722, filed on Nov. 18, 2004.

(51) Int. Cl.
| | |
|---|---|
| *C12N 15/86* | (2006.01) |
| *C07K 14/005* | (2006.01) |
| *A61K 39/21* | (2006.01) |
| *C12N 7/00* | (2006.01) |
| *A61K 39/00* | (2006.01) |

(52) U.S. Cl.
CPC ............. *C12N 15/86* (2013.01); *A61K 39/21* (2013.01); *C07K 14/005* (2013.01); *C12N 7/00* (2013.01); *A61K 2039/5256* (2013.01); *A61K 2039/575* (2013.01); *C12N 2710/10043* (2013.01); *C12N 2710/10343* (2013.01); *C12N 2710/16143* (2013.01); *C12N 2740/15034* (2013.01); *C12N 2740/15071* (2013.01); *C12N 2740/16034* (2013.01); *C12N 2740/16071* (2013.01); *C12N 2740/16134* (2013.01); *C12N 2740/16234* (2013.01); *C12N 2740/16334* (2013.01)

(58) Field of Classification Search
CPC .. A61K 39/21; A61K 2039/5256; C12N 7/00; C12N 15/86; C12N 2740/16234; C12N 2710/16143; C12N 2710/10043
See application file for complete search history.

(56) References Cited

U.S. PATENT DOCUMENTS

| | | | |
|---|---|---|---|
| 5,766,598 A | 6/1998 | Paoletti et al. | |
| 6,410,010 B1 | 6/2002 | Zhang et al. | |
| 6,511,845 B1* | 1/2003 | Davis .................. | C07K 14/005 424/199.1 |
| 6,511,847 B1 | 1/2003 | Zhang et al. | |
| 6,989,268 B2 | 1/2006 | Gregory et al. | |
| 7,157,079 B2 | 1/2007 | Nielsen et al. | |
| 2003/0157688 A1 | 8/2003 | Von Seggern et al. | |
| 2004/0170647 A1 | 9/2004 | Davis et al. | |

FOREIGN PATENT DOCUMENTS

EP 0 586 076 A2 3/1994

OTHER PUBLICATIONS

Baxi, M. K., et al., 2000, Recombinant bovine adenovirus type 3 expressing bovine viral diarrhea virus glycoprotein E2 induces an immune response in cotton rats, Virol. 278:234-243.*
Baxi et al., Recombinant bovine adenovirus type 3 expressing bovine viral diarrhea virus glycoprotein E2 induces an immune response in cotton rats, *Virol*, 2000, vol. 278, pp. 234-243.
Berget, S., et al., "Spliced segments at the 5' terminus of adenovirus 2 late mRNA," *Proc. Nat'l Acad. Sci. USA*, Aug. 1977, vol. 74, No. 8, pp. 3171-3175.
Berkner, K., et al. "Effect of the tripartite leader on synthesis of a non-viral protein in an adenovirus 5 recombinant," *Nucleic Acids Research*, 1985, vol. 13, No. 3, pp. 841-857.
Cafaro, A., et al., "Control of SHIV-89.6P-infection of cynomolgus monkeys by HIV-1 Tat protein vaccine," *Nature Medicine*, 1999, vol. 5, pp. 643-650.
Caselli, E., et al., "DNA Immunization with HIV-1 tat Mutated in the trans Activation Domain Induces Humoral and Cellular Immune Responses Against Wild-Type Tat," *The Journal of Immunology*, 1999, pp. 5631-5638.
Chanda, P., et al., "High Leval Expression of the Envelope Glycoproteins of the Human Immunodeficiency Virus Type I in Presence of rev Gene Using Helper-Independent Adenovirus Type 7 Recombinants," *Virology*, 1990, vol. 175, pp. 535-547.
Huang, W., et al., "The Tripartite Leader Sequence of Subgroup C Adenovirus Major Late mRNAs Can Increase the Efficiency of mRNA Export," *Journal of Virology*, Jan. 1998, vol. 72, No. 1, pp. 225-235.
Hutchins, "RCA Assays and Clinical Data for a rAd-p53 in Cancer Patients," BRMAC Presentation, Jul. 2001, slides 19-20.
Lee, A., et al., "Comparison of Various Expression Plasmids for the Induction of Immune Response by DNA Immunization," *Mol. Cells*, 1997, vol. 7, No. 4, pp. 495-501.
Logan, J., et al., "Adenovirus tripartite leader sequence enhances translation of mRNAs late after infection," *Proc. Natl. Acad. Sci. USA*, Jun. 1984, vol. 81, pp. 3655-3659.

(Continued)

*Primary Examiner* — Jeffrey Parkin
(74) *Attorney, Agent, or Firm* — Kilpatrick Townsend & Stockton LLP

(57) ABSTRACT

This invention provides improved replication-competent adenoviral vectors. The improved vectors have both a hybrid regulatory unit that provides for high level transgene expression. The vectors can be use, e.g., for therapeutic or prophylactic purposes.

21 Claims, 8 Drawing Sheets

(56) References Cited

OTHER PUBLICATIONS

Mason, B., et al., "Adenovirus Vaccine Vectors Expressing Hepatitis B Surface Antigen: Importance of Regulatory Elements in the Adenovirus Major Late Intron," *Virology*, 1990, vol. 177, pp. 452-461.

Massie, B., et al., "Inducible Overexpression of a Toxic Protein by an Adenovirus Vector with a Tetracycline-Regulatable Expression Cassette," *Journal of Virology*, Mar. 1998, vol. 72, No. 3, pp. 2289-2296.

Massie, B., et al., "Improved Adenovirus Vector Provides Herpes Simplex Virus Ribonucleotide Reductase R1 and R2 Subunits Very Efficiently," *Bio/Technology*, Jun. 1995, vol. 13, pp. 602-608.

Morin, J., et al., "Recombinant adenovirus induces antibody response to hepatitis B virus surface antigen in hamsters," *Proc. Natl. Acad. Sci. USA*, Jul. 1987, vol. 84, pp. 4626-4630.

Ohman, K., et al., "Two Adenovirus Proteins with Redundant Activities in Virus Growth Facilitates Tripartite Leader mRNA Accumulation," *Virology*, 1993, vol. 194, pp. 50-58.

Overell et al., Efficient gene transfer and expression in primary B lymphocytes, J. Immunol. Methods, 1991, vol. 141, No. 1, pp. 53-62 (abs).

Peng, B., et al., "Deletion of N-terminal myristoylation site of HIV Nef abrogates both MHC-1 and CD4 down-regulation," *Immunology Letter*, 2001, vol. 78, pp. 195-200.

Saito, I, et al., "Construction of Nondefective Adenovirus Type 5 Bearing a 2.8-Kilobase Hepatitis B Virus DNA Near the Right End of its Genome," *Journal of Virology*, Jun. 1985, vol. 54, No. 3, pp. 711-719.

Schmidt, E., et al., "The Cytomegalovirus Enhancer: a Pan-Active Control Element in Transgenic Mice," *Molecular and Cellular Biology*, Aug. 1990, pp. 4406-4411.

Sheay, W., et al., "Downstream Insertion of the Adenovirus Tripartite Leader Sequence Enhances Expression in Universal Eukaryotic Vectors," *BioTechniques*, 1993, vol. 15, No. 5, pp. 856-862.

Shugars, D., et al., "Analysis of Human Immunodeficiency Virus Type 1 nef Gene Sequences Present In Vivo," *Journal of Virology*, Aug. 1993, vol. 67, No. 8, pp. 4639-4650.

Soloway, P., et al., "The Adenovirus Type 5 i-Leader Open Reading Frame Functions in cis to Reduce the Half-Life of L1 mRNAs," *Journal of Virology*, Feb. 1990, vol. 64, No. 2, pp. 551-558.

Tiollais, P., et al., "Biology of Hepatitis-B Virus," *Science*, 1981, vol. 213 (4506), pp. 406-411.

Wilkinson, G., et al., "Constitutive and enhanced expression from the CMV major IE promoter in a defective adenovirus vector," *Nucleic Acids Research*, 1992, vol. 20, No. 9, pp. 2233-2239.

Wills et al., "Development and Characterization of Recombinant Adenoviruses Encoding Human p53 for Gene Therapy of Cancer," Sep. 1994, *Human Gene Therapy*, 5:1079-1088.

\* cited by examiner

SEQUENCE LISTING

```
<160> NUMBER OF SEQ ID NOS: 19

<210> SEQ ID NO 1
<211> LENGTH: 200
<212> TYPE: DNA
<213> ORGANISM: C adenovirus (Ad2)
<220> FEATURE:
<223> OTHER INFORMATION: Tpl exon 1 is from position 1 to 41; exon 2 is
      from position 42 to 113, and exon 3 is from position 114 to 200.

<400> SEQUENCE: 1
actctcttcc gcatcgctgt ctgcgagggc cagctgttgg gctcgcggtt gaggacaaac      60
tcttcgcggt ctttccagta ctcttggatc ggaaacccgt cggcctccga acgtactccg     120
ccaccgaggg acctgagcga gtccgcatcg accggatcgg aaaacctctc gagaaaggcg     180
tctaaccagt cacagtcgca                                                 200

<210> SEQ ID NO 2
<211> LENGTH: 200
<212> TYPE: DNA
<213> ORGANISM: B adenovirus (Ad7)
<220> FEATURE:
<223> OTHER INFORMATION: Tpl exon 1 is from position 1 to 41; exon 2 is
      from position 42 to 113, and exon 3 is from position 114 to 200.

<400> SEQUENCE: 2
actgtcttcc ggatcgctgt ccaggagcgc cagctgttgg gctcgcggtt gagaaggtat      60
tcttcgcgat cctccagta ctcttcgagg ggaaacccgt cttttctgc acggtactcc       120 gcgcaaggac ctgatcgtct caagatccac gggatctgaa aacctttcga cgaaagcgtc     180
taaccagtcg caatcgcaag                                                 200

<210> SEQ ID NO 3
<211> LENGTH: 33
<212> TYPE: DNA
<213> ORGANISM: Artificial
<220> FEATURE:
<223> OTHER INFORMATION: CMV5 p1 PCR Primer

<400> SEQUENCE: 3
cctctagtta tagtaatcaa ttacggggtc att                                   33

<210> SEQ ID NO 4
<211> LENGTH: 25
<212> TYPE: DNA
<213> ORGANISM: Artificial
<220> FEATURE:
<223> OTHER INFORMATION: tpl5-CMV-R PCR Primer

<400> SEQUENCE: 4
cggaagagag tcgagctctg cttat                                            25

<210> SEQ ID NO 5
<211> LENGTH: 27
<212> TYPE: DNA
<213> ORGANISM: Artificial
<220> FEATURE:
<223> OTHER INFORMATION: CMV-tpl5-F PCR Primer
```

<400> SEQUENCE: 5
gcagagctcg actctcttcc gcatcgc                                              27

<210> SEQ ID NO 6
<211> LENGTH: 27
<212> TYPE: DNA
<213> ORGANISM: Artificial
<220> FEATURE:
<223> OTHER INFORMATION: tat-tp15-R PCR Primer

<400> SEQUENCE: 6
ctacaggctc catcttgcga ctgtgac                                              27

<210> SEQ ID NO 7
<211> LENGTH: 27
<212> TYPE: DNA
<213> ORGANISM: Artificial
<220> FEATURE:
<223> OTHER INFORMATION: tp15-tat-F PCR Primer

<400> SEQUENCE: 7
gtcacagtcg caagatggag ccagtag                                              27

<210> SEQ ID NO 8
<211> LENGTH: 24
<212> TYPE: DNA
<213> ORGANISM: Artificial
<220> FEATURE:
<223> OTHER INFORMATION: Tat-polyA-F PCR Primer

<400> SEQUENCE: 8
ccgaaggaat agtgatcccc cgac                                                 24

<210> SEQ ID NO 9
<211> LENGTH: 23
<212> TYPE: DNA
<213> ORGANISM: Artificial
<220> FEATURE:
<223> OTHER INFORMATION: Tat-polyA-R PCR Primer

<400> SEQUENCE: 9
tcgggggatc actattcctt cgg                                                  23

<210> SEQ ID NO 10
<211> LENGTH: 31
<212> TYPE: DNA
<213> ORGANISM: Artificial
<220> FEATURE:
<223> OTHER INFORMATION: CMV5p2 PCR PRimer

<400> SEQUENCE: 10
cctctagatc tccgagggat ctcgaccaaa t                                         31

<210> SEQ ID NO 11
<211> LENGTH: 41
<212> TYPE: DNA
<213> ORGANISM: Artificial
<220> FEATURE:
<223> OTHER INFORMATION: Nef (WK) p1 PCR Primer

<400> SEQUENCE: 11
gcggccgcgt taacaccatg ggtggcaagt ggtcaaaacg t                              41

<210> SEQ ID NO 12
<211> LENGTH: 26

<210> SEQ ID NO 12
<211> LENGTH: 26
<212> TYPE: DNA
<213> ORGANISM: Artificial
<220> FEATURE:
<223> OTHER INFORMATION: Ad nef primer A PCR Primer

<400> SEQUENCE: 12
ttatcagcag tctttgtagt actccg                                        26

<210> SEQ ID NO 13
<211> LENGTH: 43
<212> TYPE: DNA
<213> ORGANISM: Artificial
<220> FEATURE:
<223> OTHER INFORMATION: Nef (184) primer 6 PCR Primer

<400> SEQUENCE: 13
gcggccgcgt taacaccatg aggcgagctg agccagcagc aga                     43

<210> SEQ ID NO 14
<211> LENGTH: 38
<212> TYPE: DNA
<213> ORGANISM: Artificial
<220> FEATURE:
<223> OTHER INFORMATION: CMVA7tpl7p2 PCR Primer

<400> SEQUENCE: 14
gcgatccgga agacgacagt ggatctgacg gttcacta                           38

<210> SEQ ID NO 15
<211> LENGTH: 43
<212> TYPE: DNA
<213> ORGANISM: Artificial
<220> FEATURE:
<223> OTHER INFORMATION: Ad7tplNef1p1 PCR Primer

<400> SEQUENCE: 15
cagtcgcaat cgcaaggttt aaacaccatg ggtggcaagt ggt                     43

<210> SEQ ID NO 16
<211> LENGTH: 42
<212> TYPE: DNA
<213> ORGANISM: Artificial
<220> FEATURE:
<223> OTHER INFORMATION: Ad7tplnef2p1 PCR Primer

<400> SEQUENCE: 16
cagtcgcaat cgcaaggttt aaacaccatg aggcgagctg ag                      42

<210> SEQ ID NO 17
<211> LENGTH: 35
<212> TYPE: DNA
<213> ORGANISM: Artificial
<220> FEATURE:
<223> OTHER INFORMATION: CMVA7tplp1 PCR Primer

<400> SEQUENCE: 17
tagtgaaccg tcagatccac tgtcttccgg atcgc                              35

<210> SEQ ID NO 18
<211> LENGTH: 43
<212> TYPE: DNA
<213> ORGANISM: Artificial
<220> FEATURE:
<223> OTHER INFORMATION: Ad7tplNef PCR Primer

<400> SEQUENCE: 18

```
accacttgcc acccatggtg tttaaacctt gcgattgcga ctg          43

<210> SEQ ID NO 19
<211> LENGTH: 42
<212> TYPE: DNA
<213> ORGANISM: Artificial
<220> FEATURE:
<223> OTHER INFORMATION: Ad7tplNef-2p2 PCR Primer

<400> SEQUENCE: 19
ctcagctcgc ctcatggtgt ttaaaccttg cgattgcgac tg           42
```

REPLICATION-COMPETENT ADENOVIRAL VECTORS

CROSS-REFERENCE TO RELATED APPLICATIONS

This application is a divisional of U.S. application Ser. No. 14/571,942 filed Dec. 16, 2014, now U.S. Pat. No. 9,216,214, issued Dec. 22, 2015; which is a divisional of U.S. application Ser. No. 11/282,319, filed Nov. 17, 2005, now U.S. Pat. No. 8,926,987, issued Jan. 6, 2015; which claims priority to U.S. Provisional Application No. 60/629,722, filed Nov. 18, 2004, each of which applications is herein incorporated by reference.

REFERENCE TO A SEQUENCE LISTING SUBMITTED AS AN ASCII TEXT FILE

The Sequence Listing written in file 077867-0964847-SEQLIST.txt, created on Dec. 8, 2015, 4,665 bytes, machine format IBM-PC, MS-Windows operating system, is hereby incorporated by reference.

BACKGROUND OF THE INVENTION

Adenoviruses have become important tools in vaccine development and gene transfer as vectors for in vitro, in vivo and ex vivo transfer of heterologous, therapeutic and/or immunogenic genes. Adenoviruses offer several advantages compared to other vectors; for example, they can be produced at high titers and can infect resting and nondividing cells. Furthermore, the adenoviral genome can be manipulated to accommodate foreign genes of up to about 8 kb in length. In addition, as an adenoviral vector does not insert its DNA into the chromosome of a cell, its effect is impermanent and unlikely to interfere with the cell's normal function. Lastly, live adenoviruses have been safely used as human vaccines (Horwitz, "Adenoviruses," in Virology (Fields et al., eds, Lippincott-Raven Publishers, Philadelphia, 3rd ed., pp. 2149-2171, 1996; Berkner et al., *J. Virol.*, 61, 1213-1220 (1987); Couch et al., *Amer. Rev. Respir. Dis.* 88:394-403, 1963: Franklin et al., *J. Infect. Dis.* 124:148-154, 1971; and Franklin et al., *J. Infect. Dis.* 124:155-160, 1971). Consequently, adenovirus vectors are often used to introduce a gene (or genes) of interest into a host cell.

In replication-defective Ad vectors, the E1 genes, which are required for Ad replication, are deleted. The transgene expression depends on a foreign promoter (e.g., Wilkinson & Akrigg, *Nucl. Acids Res.* 20:2233-2239, 1992; Massie, et al. *J. Virol.* 72:2289-2296, 1998). The most commonly used replication-defective Ad vector is derived from adenovirus type 5.

Unlike replication-defective Ad vector, E1 genes are maintained in replication-competent Ad vectors. In some replication competent Ad virus vectors, the viral E3 genes are deleted and a trangene is inserted downstream about 80 map unit (mu) of the adenovirus genome. The expression of the transgene is under the control of adenoviral major late promoter (MLP).

A number of gene transfer studies have employed replication-defective adenovirus vectors that have heterologous promoters to express a transgene. However, the prior art has provided conflicting reports regarding the need for a heterologous promoter for replication competent adenovirus vectors. It has been reported that the gene encoding hepatitis B virus surface antigen (HBsAg) was easily transcribed when it was incorporated into a replication competent adenovirus vector under the control of its own promoter or a heterologous promoter. However, the HBsAg mRNA was often poorly translated (e.g., Tiollais et al., *Science* 213:406, 1981; Sait et al., *J. Virol.* 54:711, 1985) and did not achieve high level expression of the protein. During the same time period, positive results were also reported for expressing the HBsAg gene without a foreign promoter (Morin, et al., *Proc. Nat. Acad. Sci. USA,* 84:4626, 1987). Thus, there was no suggestion or teaching in the art that it would be of benefit to incorporate a heterologous promoter into a replication-competent adenovirus to regulate expression of a transgene.

The current invention provides a method for achieving high level expression of a transgene using replication-competent adenovirus vectors containing a hybrid gene regulation unit. The hybrid gene regulation unit comprises a CMV promoter and an adenovirus tripartite leader sequence. These components have been incorporated into replication-defective adenoviruses to regulate transgene expression (e.g., Wilkinson & Akrigg, *Nucl. Acids Res.* 20:2233-2239, 1992; Massie, et al. *J. Virol.* 72:2289-2296, 1998). However, before the present invention, replication competent vectors comprising both the CMV and tripartite sequences were not known in the art. The present invention thus provides a new series of replication competent adenovirus vectors that comprise a hybrid regulatory unit, which provide high levels of gene expression relative to previous vectors.

In particular embodiments, the invention also provides replication competent adenovirus vectors containing a hybrid gene regulation unit that controls expression of one or more sequences encoding an HIV polypeptide. Recent advances in developing a vaccine against HIV/AIDS has led to the realization that multi-component vaccines eliciting both humoral and cellular immune responses are often important for achieving a successful vaccine. Evidence from developmental HIV and simian immunodeficiency virus (SIV) vaccine studies indicates that vaccines encoding multiple viral antigens can induce broader immune responses and/or greater protective efficacy against viral infection (e.g., Ourmanov et al., *J Virol* 74:2960-65, 2000; Kong et al., *J Virol* 77:12764-72, 2003; Hel et al., *J Immunol* 169:4778-87, 2002; Zhao et al., *J Virol* 77:8354-65, 2003; Patterson et al., *J Virol* 78:2212-21, 2004; Negri et al., *J Gen Virol* 85:1191-201, 2004; Mossman, et al., *AIDS Res Hum Retroviruses* 20:425-34, 2004.) In addition to the viral structural and enzymatic proteins, Env, Gag and Pol, viral regulatory and accessory proteins are important potential vaccine components (e.g., Robert-Guroff M. *DNA Cell Biol* 21:597-98, 2002). Tat, Rev, and Nef, in particular, have been targeted by several laboratories for vaccine development (Negri et al., Mossman et al, both supra; Osterhaus, et al., *Vaccine* 17:2713-4, 1999; Cafaro et al., *Nat Med* 5:643-50, 1999; Muthumani et al., *J Med Primatol* 31:179-85, 2002; Verrier, et al. *DNA Cell Biol* 21:653-8, 2002; Richardson et al., *DNA Cell Biol* 21:637-51, 2002; Patterson et al., *DNA Cell Biol* 21:627-35, 2002; Tikhonov et al., *J Virol.* 77:3157-66, 2003; Makitalo et al., *J Gen Virol.* 85:2407-19, 2004).

HIV-1 Tat is a small nuclear protein that has a variety of activities. In addition to functioning as a transcriptional transactivator of HIV gene expression, Tat is released from productively infected cells and can be taken up and imported into the nucleus of many different cell types. There, it promotes HIV replication or modulates the expression of cellular genes (transcription factors, cytokines, and genes that regulate the cell cycle and are important for HIV replication) (see, e.g., Barillari, et al., *Clin Microbiol Rev* 15:310-26, 2002; Caputo, et al., *Curr HIV Res,* 2004; for reviews).

Because it is produced early in the HIV replication cycle, vaccine induced immune responses to Tat might inhibit Tat functions, abrogating both HIV transactivation and the deleterious effects of Tat on uninfected, bystander cells. However, the potential use of Tat as a vaccine candidate is controversial. On the positive side, studies of HIV-infected patients and SIV-infected non-human primates suggest that an immune response to Tat has a protective role and may control the progression of the disease. Anti-Tat antibody responses and CTLs have been associated with non-progression to AIDS in infected individuals (e.g., van Baalen et al., *J Gen Virol* 78:1913-8, 1997; Re, et al., *J Clin Virol* 21:81-9, 2001; Reiss, et al., *J Med Virol* 30:163-8, 1990; Zagury, et al., *J Hum Virol* 1:282-92, 1998). Furthermore, a study in macaques infected with SIV demonstrated that anti-Tat CTLs are important to control of early virus replication (Allen, et al., *Nature* 407:386-90, 2000). As a vaccine candidate, however, mixed results have been obtained using different approaches. Immunization with active Tat protein has led to strong protection of cynomolgus macaques in pre-clinical vaccine studies (Cafaro, et al., *Nat Med* 5:643-50, 1999). In contrast, immunization with inactivated or native Tat has shown minimal or no protection of rhesus macaques (Pauza, et al., *Proc Natl Acad Sci USA* 97:3515-9, 2000; Silvera, et al., *J Virol* 76:3800-9, 2002). Thus, there is a need in the art to define the role of Tat in HIV vaccines. This invention addresses that need.

HIV Nef protein is also an attractive component of an HIV vaccine. The Nef protein is required for high-titer HIV replication in vivo and critically important for AIDS development. Nef is expressed early in the viral life cycle from the pre-integrated viral genome (Wu & Marsh, *Science* 293:1503-1506, 2001), rendering it suitable for early targeting by cellular immune responses. Nef is expressed on the surface of infected cells (Fujii, et al., *Vaccine* 11:1240-1246, 1993), and has been implicated as a target of antibody-dependent cellular cytotoxicity (Yamada, et al., *J. Immunol.* 172:2401-2406, 2004), suggesting that a vaccine elicited antibody response to Nef could also lead to rapid killing of HIV-infected cells expressing Nef.

Nef-mediated down-regulation of both CD4 (Garcia & Miller *Nature* 350: 508-511, 1991) and MHC class I (Schwartz, et al. *Nat. Med.* 2:338-342, 1996) molecules from the surface of infected cells has been well documented. These effects may affect the immunogenicity of nef-encoded vaccine candidates by diminishing the expression of Nef-peptide-MHC-I complexes on the cell surface as targets for induction of CTL responses, and by diminishing CD4 help, necessary for elicitation of both B and T-cell responses and induction of cellular memory.

The N-terminal myristoylation site of Nef is required for its association with the cell membrane. It was previously reported in in vitro studies showing that deletion of the myristoylation site prevented down modulation of both CD4 and MHC-I molecules since Nef was no longer anchored at the cell membrane (Peng & Robert-Guroff, *Immunol. Lett.* 78: 195-200, 2001). At the same time, although other regions of Nef have been shown to participate in the modulation of CD4 and MHC-1 cell surface expression and their deletion might have similarly abrogated the modulatory functions, the simple N-terminal deletion preserved almost all known Nef B- and T-cell epitopes maintaining the suitability of the mutated Nef as a vaccine candidate.

There is also a need to address the role of Nef or modified Nef forms in a vaccine. This invention provides an expression system that results in high level expression of the products of a transgene, nef. Accordingly, the invention also addresses this need.

BRIEF SUMMARY OF THE INVENTION

The invention is based on the discovery that a hybrid regulatory unit comprising a human cytomegalovirus (CMV) immediate early promoter and an adenovirus tripartite leader sequence results in greatly enhanced gene expression in replication-competent adenoviruses. Thus, the invention provides replication-competent adenovirus vectors comprising such a hybrid regulatory element that are used to express a gene of interest; expression constructs using such vectors; and methods of using such constructs, e.g., to obtain high level expression in cells.

In one aspect, the invention provides an adenovirus vector comprising a hybrid regulatory unit that controls the expression of a transgene, wherein the regulatory unit comprises a CMV immediate early promoter and a tripartite leader sequence, and further, wherein the adenovirus vector is replication-competent. The hybrid regulatory unit can be used in replication-competent adenovirus vectors, including, but not limited to adenovirus type 2, adenovirus type 4, adenovirus type 5, and adenovirus type 7. The tripartite leader sequence is often from the same strain of adenovirus, but need not be.

In some embodiments, the vector lacks sequences that are not essential for replication, e.g., the adenovirus vector can lack a functional In some instances, the vector is deleted in the E3 region. Thus, in some embodiments, the transgene is inserted into the deleted E3 region.

The vectors of the invention can be used to obtain high level expression of any gene of interest, i.e., a transgene. In one embodiment, the gene of interest is an HIV gene, such as an HIV gene that encodes a regulatory sequence or a structural protein. Exemplary HIV regulatory genes include those encoding nef or tat. Such genes can further be modified; for example, in some embodiments a nef protein encoded by a nef transgene is not myristoylated. In another exemplary embodiment, a tat encoded by the HIV regulatory gene can lack transactivation function. Exemplary HIV structural genes can encode gag or env.

The invention also provides a method of enhancing the expression of a transgene comprised by a replication-competent adenovirus vector of the invention.

The invention also provides a method of inducing an immune response to HIV, the method comprising administering an adenovirus vector of the invention that comprises a nucleic acid sequence encoding an HIV gene.

BRIEF DESCRIPTION OF THE DRAWINGS

FIG. 7A, Nef-Specific CD4 central memory cells; FIG. 7B, Nef-specific CD4 effector memory cells FIGS. 8A and 8B provide data from an exemplary analysis of Nef-specific central and effector CD8 memory T cells.

DETAILED DESCRIPTION OF THE INVENTION

Definitions

Figure 1:
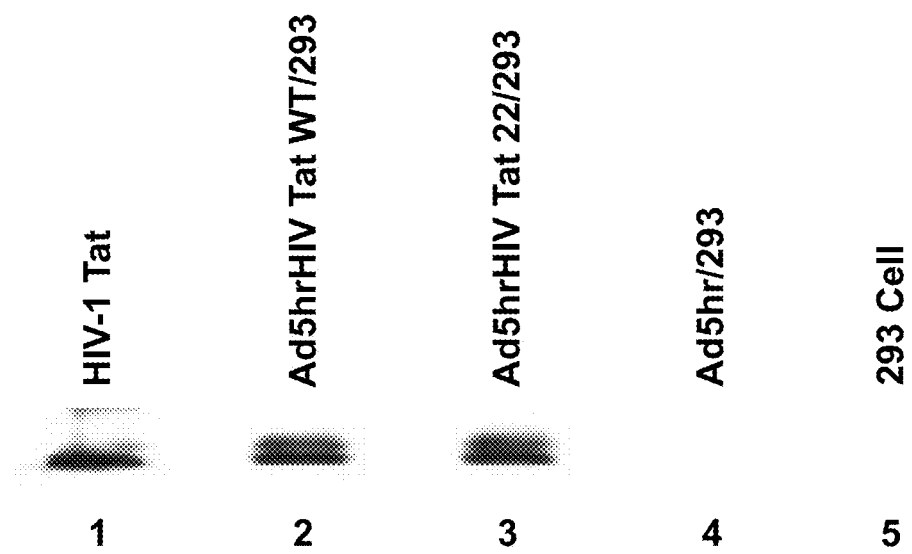
FIG. 1 provides exemplary data showing expression of HIV-1 Tat protein by Ad5hr-ΔE3-HIVtat-wt and -HIVtat22 in human cells. Human 293 cells were infected at an MOI of 10 with the Ad-recombinants or Ad5hrΔE3 vector. When 90% of the cells exhibited a cytopathic effect, lysates were prepared, separated on an SDS-polyacrylamide gel, and then transferred onto a nitrocellulose membrane. Tat expression was determined by incubating the membrane with anti-HIV-1 Tat monoclonal antibody and subsequently visualizing bands using the ECL Western blotting detection reagent. Lane 1: Recombinant HIVIIIB Tat as positive control; Lanes 2,3: Expression of Tat-WT and Tat22 following infection of 293 cells with the recombinants; Lane 4: No expression by Ad5hr-ΔE3 vector in 293 cells, negative control; Lane 5: Uninfected 293 cells, negative control FIG. 2 provides exemplary data showing that Ad5hr-ΔE3-HIVtat-wt and -HIVtat22 are immunogenic, eliciting Tat-specific cellular immunity and enhancing cellular immunity to the co-administered SIV gag immunogen. Cellular immune responses were evaluated by ELISPOT analysis of IFN-γ-secreting cells after in vitro exposure to peptide pools spanning the $HIV_{IIIB}$ Tat and SIVmac Gag proteins. Spot forming cells (SFC) are reported following subtraction of background spots observed in the presence of medium alone. Data are presented as the mean antigen-specific SFC responses±standard errors of the means. The immunization groups indicate the Ad-recombinants used for immunization. IFN-γ-secreting cells are shown after the first and second Ad-recombinant immunizations.

The term "adenovirus" or "Ad" refers to all adenoviruses, including all members of the known six subgenera, classified as A to F. Adenovirus vectors derived from an adenovirus of any of these subgenera can be used in the invention. Exemplary adenoviruses include "Adenovirus type 7" or "Ad7", which is a group B adenovirus; "Adenovirus type 4" or "Ad4", which is a group E adenovirus; and "Adenovirus type 2" or "Ad2", and "Adenovirus type 5" or "Ad5", both of which are Group C adenoviruses. Adenovirus Serotype classification is typically based on hemagglutination and resistance to neutralization by antisera to other known adenovirus serotypes. Type-specific neutralization results predominantly from antibody binding to epitopes on the virion hexon protein and the terminal knob portion of the fiber protein (see, e.g., Shenk, "Adenoviridae: The Viruses and Their Replication", pages 2111-2148, of Fields Virology, supra).

An adenovirus can be classified using a number of different methodologies (see, e.g., Shenk, supra and Horwitz, supra), typically, an immune assay and most often, a solid phase immunoassay. In current practice for specific adenovirus serotyping, the hemagglutination properties of a virus isolate are often determined, followed by serologic tests to inhibit hemagglutination or to neutralize the virus with type-specific antibodies (see, e.g., Horwitz, supra). Other immune assays can also be used to type an adenovirus. For example, an adenovirus type can be determined using type-specific antibodies to epitopes on the hexon or fiber protein of adenovirus, often the fiber protein, using an assay such as immunofluorescence to detect specific binding of the antibody to the epitope. "Specific binding" refers to a binding reaction that is determinative of the presence of a protein in a mixture. Thus, under designated immunoassay conditions, the specified antibodies bind to a particular adenovirus hexon or fiber protein and do not substantially bind in a significant amount to other proteins, including other adenoviral capsid proteins. Typically a specific or selective reaction will provide a signal that is at least 10 to 100 times background binding to other proteins.

"Replication defective", "replication incompetent", or "replication deficient" are used interchangeably in this application to refer to an adenoviral genome that does not comprise all of the genetic information for the virus to replicate in cells that are not capable of complementing deleted adenoviral functions. For example, recombinant adenoviral vectors possessing a deletion of E1 gene functions are essentially unable to replicate except in cell lines that have been engineered to complement E1 functions.

A "replication competent" adenovirus includes the genetic information that allows the adenovirus to replicate in cells. Such a vector may lack other regions of the genome, e.g., E3 or E4.

The term "heterologous" when used with reference to a nucleic acid, indicates that the nucleic acid is in a vector, a cell, or a virus where it is not normally found in nature; or, comprises two or more subsequences that are not found in the same relationship to each other as normally found in nature, or is recombinantly engineered so that its level of expression, or physical relationship to other nucleic acids or other molecules in a cell, or structure, is not normally found in nature. For instance, a heterologous nucleic acid is typically recombinantly produced, having two or more sequences from unrelated genes arranged in a manner not found in nature: e.g., an HIV gene operatively linked to a promoter sequence inserted into an adenovirus-based vector of the invention.

The term "expression cassette" refers to a series of nucleic acid sequence elements that permit transcription of a gene or polynucleotide in a host cell. In addition to regulatory regions such as the CMV promoter and tripartite leader, expression cassettes can also include other components, e.g., transcription termination signals, polyadenylation signals, and the like. Falling within the definition of "expression cassette" are "expression vectors," "cloning vectors," "viral vectors," and the like, all terms which usually refer to viruses, plasmids or other nucleic acid molecules that are able to transduce and/or replicate in a chosen host cell.

A "gene" that is expressed by a vector of the invention refers to a nucleic acid encoding a full-length transcript or a fragment thereof. For example, a "gene" may encode a full-length polypeptide, or a portion of the polypeptide, such as an epitope. "Polypeptide" is used interchangeably with "peptide" or "protein" in the current invention. In some embodiments, e.g., vaccines, a polypeptide can also be referred to as an "antigen".

The terms "identical" or percent "identity," in the context of two or more nucleic acids (or polypeptide sequences), refer to two or more sequences or subsequences that are the same or have a specified percentage of nucleotides (or amino acid residues) that are the same (i.e., about 70% identity, preferably 75%, 80%, 85%, 90%, 91%, 92%, 93%, 94%, 95%, 96%, 97%, 98%, 99%, or higher identity over a specified region (e.g., SEQ ID NO:1 or 2), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or can be applied to, the complement of a test sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 nucleotides (or amino acids) in length, and oftentimes over a region that is 225, 250, 300, 350, 400, 450, or 500 or more nucleotides (or amino acids) in length, or over the full-length of a reference sequence.

For sequence comparison, typically one sequence acts as a reference sequence, to which test sequences are compared. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 are used, with the parameters described herein, to determine percent sequence identity in the context of this invention. Software for performing BLAST analyses is publicly available through the National Center for Biotechnology Information. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4 and a comparison of both strands.

A "transgene" as used herein refers to a heterologous gene encoding a transcript of interest that is introduced into a vector.

"Pharmaceutically acceptable" refers to a non-toxic, inert, and/or physiologically compatible composition.

A "pharmaceutical excipient" comprises a material such as an adjuvant, a carrier, pH-adjusting and buffering agents, tonicity adjusting agents, wetting agents, preservative, and the like.

INTRODUCTION

The invention provides gene transfer vectors that provide high level expression of transgenes, e.g., in vivo. The vectors of the invention are replication competent adenoviral vectors having a hybrid regulatory unit comprising a CMV promoter and an adenovirus tripartite leader (tpl) sequence. This regulatory unit controls expression of one or more genes of interest incorporated into the vector such that the transgene(s) is operably linked to the regulatory unit. The vectors can be used for many applications, e.g., to express proteins at high levels to provide a source of the protein, as well as for therapeutic or prophylactic applications.

The present vectors are more effective in comparison to existing replication-defective adenoviruses that incorporate a CMV promoter and tpl sequences. To achieve the desired gene expression level using replication-defective adenovirus, high doses are usually used in vivo. However, such a high dose tends to cause adverse immunopathology. In replication-competent adenovirus vectors, higher gene expression is obtained in vivo, as there are a greater number of DNA templates available during adenovirus vector replication. Therefore, less adenovirus is needed for immunization. Further, in vivo replication of adenovirus vectors stimulate the production of pro-inflammatory cytokines that augment immune response.

Not to be bound by theory, in the vectors of the invention, enhancement of transgene expression relates to two factors: the CMV promoter constitutively produces a large amount of tpl-containing mRNA of transgenes; and the adenovirus viral major late promoter provides adenovirus-related mRNA containing tpl-containing transgenes in every adenovirus replication cycle. Thus, tpl-containing mRNA of transgenes are significantly increased and transgene expression is more efficient than in replication-competent vectors lacking the CMV promoter.

The transgene controlled by the hybrid regulatory unit can be expressed in adenovirus non-permissive cells and the invention can be adapted to different serotypes of replication-competent adenoviruses.

Expression Vector Components
Tripartite Leader (tpl) Nucleic Acid Sequences

One of the components of the hybrid regulatory unit to be used in the replication-competent adenovirus vectors of the invention comprises a sequence encoding an adenovirus tripartite leader sequence (e.g., Logan & Schenk, *Proc. Natl. Acad. Sci. USA* 81:3655-3659, 1984; Huang & Flint, *J. Virol.* 72:225-235, 19998). The tripartite leader sequence is an untranslated 5' sequence present in all viral mRNAs processed from major late transcripts. Sequences containing the tpl bind translation-initiating proteins more efficiently than many mRNAs that lack the sequence.

In human adenoviruses, the late transcription unit is transcribed from a major late promoter located (in group C adenoviruses) at 16.3 mu and continues to the right end of the genome. The primary transcript is processed to about 20 late mRNAs that comprise five families (L1 to L5) of mRNAs. As noted above, the mRNAs transcribed from the MLP contain an identical 5' non-coding segment of about 150-200 nt in length, the tpl. It is derived from the splicing of three small exons located at 16.3, 19.0, and 26 mu. An exemplary tpl is from human adenovirus type 2. The overall length of the tpl from human Ad2 is 201 nt, with its first exon of 41 nt from the MLP region (16.2 mu), its second exon of 71 nt from the DNA Pol region (19.6 mu), and its third exon of 89 nt from the pTP region (26.3 mu) of the genome.

As encoded in adenovirus DNA, the tripartite leader is interrupted by large introns. The presence of these introns or portions of the introns does not adversely affect expression levels. Accordingly, the vectors of the invention can comprise intron sequences that separate one or more exons of the tpl. For example, in some embodiments a native tripartite leader intron, e.g, intron 1, may be included in a construct of the invention. However, in many embodiments, the tpl is a spliced tripartite leader sequence (e.g., Berg et al., *Bio Techniques* 14:972-978). The tpl exons are typically from Ad2, Ad4, Ad5, or Ad7, but may come from any adenovirus serotype. Exemplary sequences are found, e.g., in US application no. 2003/0157588, U.S. Pat. No. 6,511,845, and other references available in the art.

An exemplary tpl from a group C adenovirus (Ad2) is provided below. The sequence is presented as the spliced tpl, shown 5' to 3'.

```
                                          (SEQ ID NO: 1)
ACTCTCTTCC GCATCGCTGT CTGCGAGGGC CAGCTGTTGG

GCTCGCGGTT GAGGACAAAC TCTTCGCGGT CTTTCCAGTA

CTCTTGGATC GGAAACCCGT CGGCCTCCGA ACGTACTCCG

CCACCGAGGG ACCTGAGCGA GTCCGCATCGA CCGGATCGGA

AAACCTCTCG AGAAAGGCGT CTAACCAGTC ACAGTCGCA
```

Tpl exon 1 is from position 1 to 41; exon 2 is from position 42 to 113, and exon 3 is from position 114 to 200.

An exemplary sequence tpl from a group B adenovirus (Ad7) is shown below, 5' to 3':

```
                                          (SEQ ID NO: 2)
ACTGTCTTCC GGATCGCTGT CCAGGAGCGC CAGCTGTTGG

GCTCGCGGTT GAGAAGGTATTCTTCGCGAT CCTTCCAGTA

CTCTTCGAGG GGAAACCCGT CTTTTTCTGC

ACGGTACTCCGCGCAAGGAC CTGATCGTCT CAAGATCCAC

GGGATCTGAA AACCTTTCGA CGAAAGCGTCTAACCAGTCG

CAATCGCAAG
```

Tpl exon 1 is from position 1 to 41; exon 2 is from position 42 to 113 and exon 3 is from position 114 to 200. This tpl is 78% identical to the Ad2 tpl shown above.

In other embodiments, the tpl is from adenovirus type 5. The tpl in adenovirus type 5 is almost identical to that of adenovirus type 2, differing at one position.

One of skill in the art can readily identify tpl sequences from any adenovirus strains based on sequence conservation with known tpl sequences. For example, Hsaio et al., (*Gene* 89:275-277, 1990) identified the tripartite leader sequences of the simian adenovirus type 30 based on sequence homology with human adenovirus tpl. This sequence exhibits 74% identity with the Ad2 tpl. Other variants can also be produced for use in the invention. For example, such variants can be generated based on sequences that are conserved among adenovirus strains, e.g., human adenovirus strains. Variant tpl sequences often have at least 70% identity, frequently 75%, 80% identity, 90%, or 95% or greater, sequence identity to an Ad2, Ad5, or Ad7 spliced tpl. Such variants typically retain residues that are conserved between aligned tpl sequences, e.g., the Ad2 and Ad7 tpl sequences.

Variants can also comprise a partial tpl exon, e.g., a partial exon 1 (e.g., US Patent Application No 20030157688). A tpl can be evaluated for function using various known assays (see, e.g., Logan & Schenk, *Proc. Natl. Acad. Sci. USA* 81:3655-3659, 1984; Huang & Flint, *J. Virol.* 72:225-235, 19998) or by comparing its potency to an exemplary tpl, e.g., Ad2 tpl, in an expression system.

As noted above, the expression unit may also comprise one or more introns. For example, an intron may be included in the tpl segment of the expression unit. Such an intron and tpl exons can be operatively linked in a variety of configurations to provide a functional tpl nucleotide sequence. For example, the intron can be positioned between any of tpl exons 1, 2 or 3; preceding the first tpl exon or following the last tpl exon. Further the tpl exons can be in any order.

CMV Immediate Early Promoter

The second component of the hybrid regulatory unit for use in the invention is a CMV immediate early promoter. The term "CMV promoter" or "CMV immediate early promoter" as used herein refers to the immediate-early promoter-regulatory region from human cytomegalovirus, including the enhancer region. The human cytomegalovirus genome contains a region upstream of the major IE gene (IE1) that can strongly bind host cell transcription factors. This region is referred to as the major IE enhancer-containing promote regulatory region (see, e.g., U.S. Pat. Nos. 5,168,062 and 5,385,839; Isomura *J. Virol.* 78:12788-12799, 2004; Stinski, et al., pages 2465-2469, in Fields, Virology Vol. 2. Third Edition, 1996, Lippincott, Williams and Wilkins, publishers) and Meier et al., *J. Virol.* 76:313-326, 2002 and references cited therein). The adenoviral vectors of the invention comprise a cloning site, which allows the heterologous sequence cloned into the site to be controlled by the CMV promoter. The CMV promoter is located upstream of a tripartite leader sequence.

The CMV promoter is one of the strongest enhancer/promoters known and is active in abroad range of cell types (see, e.g., Chapman et al., *Nuc. Acids Res.* 19:3979-3986, 1991; and U.S. Pat. No. 5,688,688). The strength of the CMV promoter lies primarily in its enhancer element, which contains multiple binding sites for transcription factors. Accordingly, a CMV promoter for use in this invention comprises elements contained within the enhancer. The human CMV enhancer is divided into three regions that influence gene expression, the fartheset upstream domain, the adjacent region, and the domain between about −500 and the transcription start site. The human CMV enhancer between positions −550 and −39 relative to the +1 start site of the immediate early gene multiple repetitive elements containing transcription factor binding sites. For example, there are at least four types of repetitive sequence elements, often referred to as the 16-, 18-, 19-, and 21-bp repeats, which are present three to five times within the promoter/enhancer region of the CMV promoter. These (and other sequences) form complexes with nuclear proteins. The 18- and 19-bp repeats contain consensus binding sites for NFB and CREB/ATF, respectively, and have been shown to mediate the enhancement of CMV promoter activity by these transcription factors. These repeated elements are conserved in the murine and simian CMV enhancers. Other factors that bind to the CMV promoter are AP-1, SP 1, and MDBP. Additionally, the promoter can be stimulated in trans by the product of the adenovirus E1a gene.

The invention also encompasses the use of variant CMV promoters that exhibit the same function in controlling immediate early gene expression as the Towne strain CMV promoter that is often used. Such promoters can be identified by their position and function. For example, the promoter from human CMV strain AD169 can also be used. Functionality can readily be assessed by comparing the variants to a native CMV promoter using common transcription assays. Accordingly, the term "CMV promoter" encompasses variants of the human CMV IE promoter-enhancer Towne strain. CMV variants conserve transcription factor binding sites, e.g., the repetitive sequences noted above. CMV promoters used in the invention typically have CMV enhancer and CMV basal promoter sequences, but in some embodiments, may employ basal promoter regions comprising elements such as a TATAA and a CAAT box from sources other than the a human cytomegalovirus. Exemplary Towne strain sequences are provided, e.g., in U.S. Pat. No. 5,168,062, Isomura, et al. and Meier, et al., both supra). Variant CMV promoters thus typically share substantial sequence identity, e.g., at least 70%, 75%, 80%, 85%, 90%, 95%, or greater, with the enhancer region of the Towne strain CMV promoter between positions −550 and −39 relative to the +1 start site of the immediate early gene.

Gene of Interest

The expression vectors of the invention can be used to express any gene of interest. Such genes include those for eliciting an immune response, e.g., genes from infectious disease agents, cancer-related genes, and the like. The vectors can be particularly useful for expression of proteins that are small, e.g., about 300 amino acids or less in length, often about 200 amino acids or less in length. In some embodiments, the vectors are used to express viral genes, such as retroviral genes or genes from other viruses. In exemplary embodiments, the constructs are used to express retroviral genes.

Antigenic polypeptide sequences for provoking an immune response selective for a specific retroviral pathogen are known. With minor exceptions, the following discussion of HIV epitopes/immunogenic polypeptides is applicable to other retroviruses, e.g., SIV, except for the differences in sizes of the respective viral proteins. HIV antigens for a multitude of HIV-1 and HIV-2 isolates, including members of the various genetic subtypes of HIV, are known and reported (see, e.g., Myers et al., Los Alamos Database, Los Alamos National Laboratory, Los Alamos, N. Mex. (1992)) and antigens derived from any of these isolates can be used in the methods of this invention. Immunogenic proteins can be derived from any of the various HIV isolates, or consensus sequences from isolates, including any of the various envelope proteins such as gp120, gp160 and gp41; gag antigens such as p24gag and p55gag, as well as proteins derived from pol, tat, vif, rev, nef, vpr, vpu.

Replication Competent Adenovirus Vectors

A replication-competent adenovirus vector retains the genetic material in the vector that is required for replication in a host cell. Such vectors may, however, harbor deletions or mutations in other regions of the adenovirus. For example, the E3 region can be deleted (partially or wholly) without affecting the ability to replicate. Accordingly E3-deleted (or otherwise mutated) vectors that lack E3 function can be used in the invention. Other regions that may be deleted or mutated include E4 (see. e.g., U.S. Pat. No. 6,093,567).

Replication-competent adenoviruses require no trans complementation and can grow on various standard human cell lines, including A549, WI-38, MRC-5, HeLa, etc. They will also grow on 293 cells and similar cells containing the Ad5 E1 genes. Accordingly, an engineered adenovirus can be evaluated for replication competence by assaying growth on cell lines such as these exemplary cell lines.

Formulation and Administration of Pharmaceuticals

As discussed above, the present invention also provides recombinant replication-competent adenovirus vectors for use in vaccines and as gene transfer vectors. The adenovirus prepared as described herein can be formulated for administration to a mammalian organism in accordance with techniques well known in the art. The viruses can be administered in conventional solutions such as sterile saline and can incorporate one or more pharmaceutically acceptable carriers or excipient to form a pharmacological composition. The pharmaceutical composition can further comprise other active agents, including other recombinant viruses, plasmids, naked DNA or other agents.

The compositions for administration typically comprise a buffered solution comprising adenovirus in a pharmaceutically acceptable carrier, e.g., an aqueous carrier. A variety of carriers can be used, such as buffered saline, water and the like. These solutions are generally sterile and free of undesirable matter. These compositions can be sterilized by conventional, well known sterilization techniques, or can be sterile filtered. The compositions may contain pharmaceutically acceptable auxiliary substances as required to approximate physiological conditions such as pH adjusting and buffering agents, tonicity adjusting agents and the like, for example, sodium acetate, sodium chloride, potassium chloride, calcium chloride, sodium lactate and the like.

Pharmaceutically acceptable carriers can contain a physiologically acceptable compound that acts, e.g., to stabilize the composition or to increase or decrease the absorption of the virus and/or pharmaceutical composition. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of any co-administered agents, or excipient, or other stabilizers and/or buffers. Detergents can also be used to stabilize the composition or to increase or decrease absorption.

The adenovirus constructs can also be administered in a lipid formulation, more particularly either complexed with liposomes or to lipid/nucliec acid complexes (e.g., WO 93/24640; U.S. Pat. No. 5,279,833, and WO 91/06309) or encapsulated in liposomes, as in immunoliposomes directed to specific tumor markers.

The adenovirus constructs of the invention can also be administered orally as enteric coated capsules as previously described, in order to bypass the upper respiratory tract and replicate in the gut: see, e.g., Tacket et al., *Vaccine* 10:673-676, 1992; Horwitz, in Fields et al., eds., *Fields Virology*, third edition, vol 2, pp. 2149-2171, 1996; Takafuji et al., *J. Infec. Dis.* 140:48-53, 1979; and Top et al., *J. Infec. Dis.* 124:155-160, 1971.

One skilled in the art would appreciate that the choice of a pharmaceutically acceptable carrier, including a physiologically acceptable compound depends, e.g., on the route of administration of the adenoviral preparation and on the particular physio-chemical characteristics of any co-administered agent.

In some embodiments of the invention, the targeted complexes of the invention are administered ex vivo to cells or tissues explanted from a patient, then returned to the patient. Examples of ex vivo administration of therapeutic gene constructs include Arteaga et al., *Cancer Research* 56(5):1098-1103 (1996); Nolta et al. *Proc. Nat'l. Acad. Sci. USA* 93(6):2414-9 (1996); Koc et al., *Seminars in Oncology* 23 (1):46-65 (1996); Raper et al., *Annals of Surgery* 223(2): 116-26 (1996); Dalesandro et al., *J. Thorac. Cardi. Surg.*, 11(2):416-22 (1996); and Makarov et al., *Proc. Nat'l. Acad. Sci. USA* 93(1):402-6 (1996).

Administration

The compositions can be administered alone, or can be co-administered or sequentially administered with other immunological, antigenic, vaccine, or therapeutic compositions. Such compositions can include other agents to potentiate or broaden the immune response, e.g., IL-2 or other cytokines which can be administered at specified intervals of time, or continuously administered (see, e.g., Smith et al., *N Engl J Med* 1997 Apr. 24; 336(17):1260-1; and Smith, *Cancer J Sci Am.* 1997 December; 3 Suppl 1:S137-40). The vaccines or vectors can also be administered in conjunction with other vaccines or vectors. For example, an adenovirus of the invention can be administered either before or after administration of an adenovirus of a different serotype. An adenovirus preparation may also be used, for example, for priming in a vaccine regimen using an additional vaccine agent.

The adenoviral formulations can be delivered systemically, regionally, or locally. Regional administration refers to administration into a specific anatomical space, such as intraperitoneal, intrathecal, subdural, or to a specific organ, and the like. Local administration refers to administration of a composition into a limited, or circumscribed, anatomic space such as an intratumor injection into a tumor mass, subcutaneous injections, intramuscular injections, and the like. One of skill appreciates that local administration or regional administration can also result in entry of the viral preparation into the circulatory system. Typical delivery routes include parenteral administration, e.g., intradermal, intramuscular or subcutaneous routes. Other routes include oral administration, intranasal, and intravaginal routes. For delivery of adenovirus, administration can often be performed via inhalation.

The vectors of the current invention, alone or in combination with other suitable components can be made into aerosol formulations to be administered via inhalation. These aerosol formulations can, for example, be placed into pressurized, pharmaceutically acceptable propellants, such as dichlorodifluoromethane, nitrogen and the like. They can also be formulated as pharmaceuticals for non-pressurized preparations such as in a nebulizer or an atomizer. Typically, such administration is in an aqueous pharmacologically acceptable buffer as described above. Delivery to the lung can also be accomplished, for example, using a bronchoscope.

The vaccines can also be formulated for administration via the nasal passages. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. For further discussions of nasal administration of AIDS-related vaccines, references are made to the following patents, U.S. Pat. Nos. 5,846,978, 5,663,169, 5,578,597, 5,502,060, 5,476,874, 5,413,999, 5,308,854, 5,192,668, and 5,187,074.

Formulations for oral administration can consist of liquid solutions, such as an effective amount of the pharmaceutical dissolved in ingestible diluents, such as water, saline, orange juice, and the like; capsules, or tablets containing a predetermined amount of the active ingredient; suspensions in an appropriate liquid; and suitable emulsions.

Additionally, the vectors can be made into suppositories by mixing with a variety of bases such as emulsifying bases or water-soluble bases. Formulations suitable for vaginal administration can be presented as pessaries, tampons, creams, gels, pastes, foams, or spray formulas.

The pharmaceutical formulations of the invention can be administered in a variety of unit dosage forms, depending upon the intended use, e.g., prophylactic vaccine or therapeutic regimen, and the route of administration, With regard to therapeutic use, the particular condition or disease and the general medical condition of each patient will influence the dosing regimen. The concentration of adenovirus in the pharmaceutically acceptable excipient can be, e.g., from about $10^5$ to about $10^{12}$ particles per mL or between about $10^6$ to about $10^9$ particles per ml, or between about $10^7$ to about $10^8$ particles per mL in an aqueous solution.

The replication-competent adenovirus recombinants of the invention are typically administered at much lower doses than would be needed to achieve equivalent expression levels of the encoded transgene by a replication-defective adenovirus recombinant administered in vivo. Replication competent adenovirus vectors can be administered at a range of dosages (see, e.g., U.S. Pat. No. 4,920,209; Smith et al., *J. Infec. Dis.* 122:239-248, 1970; Top et al., *J. Infec. Dis.* 124:155-160, 1971; Takafuji et al., *J. Infec. Dis.* 140:48-53, 1979; Tacket et al., *Vaccine* 10:673-676, 1992). For example, $10^4$ to $10^9$ 50% tissue culture infective doses (or plaque forming units) can be administered. Typically an oral dosage for a replication-competent adenovirus is about $10^7$ 50% tissue culture infective doses or $10^7$ plaque forming units. Typical intranasal administration of adenovirus recombinants is often in dosages of about $10^4$ to about $10^5$ plaque forming units. The exact concentration of virus, the amount of formulation, and the frequency of administration can also be adjusted depending on the levels of in vivo, e.g., in situ transgene expression and vector retention after an initial administration. Details on dosages are well described in the scientific and patent literatures, see, e.g., the latest edition of Remington's Pharmaceutical Sciences; Sterman et al., *Hum. Gene Ther* 9:1083-1092, 1998; and Smith et al. *Hum. Gene Ther.* 8:943-954, 1997.

The amount and concentration of virus and the formulation of a given dose, or a "therapeutically effective" dose is determined by the clinician as discussed herein. A therapeutically effective dose of a vaccine is an amount of adenovirus that will stimulate an immune response to the protein(s) encoded by the heterologous nucleic acid included in the viral vector. For gene therapy, a therapeutically effective dose can be an amount sufficient to reduce or otherwise alleviate symptoms of a disease.

The dosage schedule, i.e., the dosing regimen, will depend upon a variety of factors, e.g., the stage and severity of the disease or condition to be treated, and the general state of the patient's health, physical status, age and the like. The state of the art allows the clinician to determine the dosage regimen for each individual patient. Adenoviruses have been safely used for many years for human vaccines; see, e.g., Franklin et al., supra; Jag-Ahmade et al., *J. Virol.,* 57:267, 1986; Ballay et al, *EMBO J.* 4:3861, 1985; PCT publication WO 94/17832. They have also been used in humans as in vivo gene delivery vehicles (e.g., Graham & Prevec in *New Approaches to Immunological Problems*, Ellis Ted), Butter worth-Heinemann, Boston, Mass., pp. 363-390, 1992; Rago et al, *Nature* 361:647-650, 1993; Kozarsky, *Curr. Opin. Genet. Dev.* 3:499-503, 1993; and U.S. Pat. Nos. 5,981,225, and 5,837,511). These illustrative examples can also be used as guidance to determine the dosage regimen when practicing the methods of the invention.

Single or multiple administrations of adenoviral formulations can be administered, either as prophylactic vaccines or as therapeutic regimens. In the latter case, the dosage and frequency are adjusted as required and tolerated by the patient. One typical dosage for regional, e.g., intranasal administrations is between about 0.2 to about 1.0 mL of a formulation with about $10^4$ viral particles per mL. In an alternative embodiment, oral administration can include of about $10^7$ to about $10^9$ viral particles per mL, lyophilized and formulated into an enteric-coated tablet. Lower dosages can be used, such as tablets of a formulation with about $10^5$ viral particles per mL.

Kits

The invention also provides kits that contain the vectors, vector systems or pharmaceutical compositions of the invention. The kits can, for example, also contain cells for growing the adenoviruses of the invention. The kits can also include instructional material teaching methodologies for generating adenoviruses using the kits and, for pharmaceutical compositions, can include instruction for indication of dosages, routes and methods of administration and the like.

EXAMPLES

Example 1. Immunogenics of Replication Competent Adenovirus Type 5 Vectors Expressing Tat Materials and Methods
Adenovirus Type 5 Host Range (Ad5hr) Recombinants A replication competent Ad5hr-SIV recombinant carrying the SIVmac239 gag gene was described previously (Zhao, et al., *Vaccine* 21:4002-35, 2003). Plasmids pBRAd5ΔE3 and pAd5tpl5-18RD2 used for construction of Ad5hr-HIV-1tat-wt and Ad5hr-HIV-1tat$_{22}$ recombinants were obtained from Wyeth-Lederle Vaccines under a Cooperative Research and Development Agreement. The vector pBRAd5ΔE3 contains the Ad5 sequence from 59.5 to 100 map units (mu) in which the E3 region from 78.8 to 85.7 mu is deleted. Plasmid pCI vector containing CMV and polyA was purchased from Promega (Madison, Wis.). Ad5hr-recombinants carrying HIVtat-wt and the transdominant mutant tat$_{22}$ (Cys22 to Gly) were constructed as follows. First, the CMV promoter, the tpl of the Ad5 serotype (tpl5), tat-wt (or tat$_{22}$), and polyA were amplified separately by PCR with four pairs of primers:

```
CMV5 p1 (5' to 3'):
                                        (SEQ ID NO: 3)
CCTCTAGTTATAGTAATCAATTACGGGGTCATT
and tp15-CMV-R
                                        (SEQ ID NO: 4)
CGGAAGAGAGTCGAGCTCTGCTTAT;

CMV-tp15-F:
                                        (SEQ ID NO: 5)
GCAGAGCTCGACTCTCTTCCGCATCGC;
and tat-tp15-R:
                                        (SEQ ID NO: 6)
CTACAGGCTCCATCTTGCGACTGTGAC;

tp15-tat-F
                                        (SEQ ID NO: 7)
GTCACAGTCGCAAGATGGAGCCAGTAG
and Tat-polyA-F:
                                        (SEQ ID NO: 8)
CCGAAGGAATAGTGATCCCCCGAC;
and Tat-polyA-R:
                                        (SEQ ID NO: 9)
TCGGGGGATCACTATTCCTTCGG
and CMV5p2
                                        (SEQ ID NO: 10)
CCTCTAGATCTCCGAGGGATCTCGACCAAAT.
```

Secondly, a hybrid expression cassette of CMV-Ad5tpl-Tat-wt (or Tat$_{22}$)-polyA was assembled by PCR using a mixture of the above PCR products as template and the primer pair CMV5 p1 and CMV5 p2. The amplified expression cassette was then inserted into the Xba1 site at 78.8 mu of pBRAd5ΔE3. The correct gene orientation and sequence of both pBRAd5ΔE3HIV-1tat-wt and pBRAd5ΔE3HIV-1tat$_{22}$ were confirmed by DNA sequencing. The Ad5hr-HIV-1tat-wt recombinant was generated by homologous recombination between Ad5hr viral DNA, 1 to 76 mu, and pBRAd5ΔE3HIV-1tat-wt as described previously (Zhao, et al., *Vaccine* 21:4002-35, 2003). The Ad5hr-HIV-1tat$_{22}$ recombinant was similarly constructed by homologous recombination between Ad5hr viral DNA, 1 to 76 mu, and pBRAd5ΔE3HIV-1tat$_{22}$.

Expression of the Tat protein in human 293 cells infected with the Ad5hr-HIV-1 tat-wt or HIV-1tat$_{22}$ recombinants was evaluated by Western blot. The 293 cells were infected at an MOI of 10 with the recombinants or the Ad5hrΔE3 vector as negative control. When 90% of the cells exhibited a cytopathic effect, cell lysates were prepared with radioimmunoprecipitation assay buffer (50 mM Tris-HCl, pH 8.0, containing 150 mM NaCl, 1% polyethoxyethanol (Sigma, St. Louis, Mo.), 0.5% sodium deoxycholate, 0.1% sodium dodecyl sulfate (SDS), and 1 mM phenylmethylsulfonyl fluoride), separated on an SDS-polyacrylamide gradient gel of 4-20% (Bio-Rad), and then transferred onto a nitrocellulose membrane (Bio-Rad). Tat expression was determined by incubating the membrane with anti-HIV-1 Tat monoclonal antibody (NT3 2D1.1; AIDS Research and Reference Reagent Program, NIAID, NIH) and subsequently visualizing bands using the ECL Western blotting detection reagent (Amersham Pharmacia Biotech, Piscataway, N.J.), as described by the manufacturer.

Immunization of Mice and Sample Collection

Female Balb/C mice at 6-8 weeks of age were used in this study. Each group included 10 mice except groups VII and VIII that contained 5 mice each. The immunization schedule is outlined in Table 1. Each Ad-recombinant was administrated intraperitoneally at $10^8$ plaque-forming units (pfu) per immunization in a total volume of 500 μl phosphate-buffered saline (PBS) regardless of the number of recombinants given. Five mice per group in groups I-VI were sacrificed two weeks after the first immunization and 5 mice per group in groups I-VIII were sacrificed after the second immunization at week 4. Spleens and blood were collected to evaluate immune responses. Mouse splenocytes were isolated by passing spleen fragments through a 70 μm nylon cell strainer. After lysis of erythrocytes, the splenocytes were resuspended in R-10 medium (RPMI-1640 containing 10% FCS, 2 mM L-glutamine, 25 mM HEPES, 100 U/ml penicillin, and 100 μg/ml streptomycin).

TABLE 1

Mouse immunization schedule.

| Group | Immunogens | # Mice Immunized Wk 0 | # Mice Sacrificed Wk 2 | # Mice Immunized Wk 4 | # Mice Sacrificed Wk 6 |
|---|---|---|---|---|---|
| I | Ad5hrΔE3-HIVtat-wt | 10 | 5 | 5 | 5 |
| II | Ad5hrΔE3-HIVtat22 | 10 | 5 | 5 | 5 |
| III | Ad5hrΔE3-SIVgag | 10 | 5 | 5 | 5 |
| IV | Ad5hrΔE3-HIVtat-wt + Ad5hrΔE3-SIVgag | 10 | 5 | 5 | 5 |
| V | Ad5hrΔE3-HIVtat22 + Ad5hrΔE3-SIVgag | 10 | 5 | 5 | 5 |
| VI | Ad5hrΔE3 Vector | 10 | 5 | 5 | 5 |
| VII | Ad5hrΔE3-HIVtat-wt | 5 | 0 | | |
| VIII | Ad5hrΔE3-HIVtat-wt + Ad5hrΔE3-SIVgag | 0 | | 5 | 5 |
| | Ad5hrΔE3-HIVtat22 | 5 | 0 | | |
| | Ad5hrΔE3-HIVtat22 + Ad5hrΔE3-SIVgag | 0 | | 5 | 5 |

ELISPOT Assay

IFN-γ secretion in response to SIV Gag, HIV-1 Tat, and Ad5 fiber peptides was evaluated by ELISPOT assay. Gag peptides included fifty 20-mer peptides with 10-amino acid overlap, spanning the entire SIVmac239 Gag protein. HIV-1 Clade B consensus Tat peptides included twenty-three 15-mer peptides with 11-amino acid overlap. Both SIV Gag and HIV-1 Tat peptides were obtained from the AIDS Research and Reference Reagent Program, NIAID, NIH. The ELISPOT assay for the Th-1 cytokine IFN-γ was performed using commercial kits (U-Cytech, Utrecht, The Netherlands) according to the manufacturer's manual with slight modification. Briefly, 96-well flat-bottom plates were coated overnight with anti-IFN-γ monoclonal antibody MD-1 (U-Cytech), washed and blocked as described. Dilutions of splenocytes ranging from $2 \times 10^5$ to $0.25 \times 10^5$ per 100 μl R-10 medium were transferred to triplicate wells, together with 2 μg/ml of each peptide in the Gag, Tat and Ad5 Fiber peptide pools. Concanavalin A (Con A) (Sigma) at 5 μg/ml and R-10 medium alone were used as positive and negative controls. Following overnight incubation at 37° C. in 5% $CO_2$, the cells were removed, and the wells washed and incubated with biotinylated anti-IFN-γ antibody (U-Cytech). After further washing, bound anti-IFN-γ antibody was detected with a gold-labeled anti-biotin solution (U-Cytech). Spots were developed by incubating the plates with U-Cytech's activator mixture. The color reaction was stopped by washing with distilled water. The plates were air-dried, and spots were counted visually using an inverted microscope.

T-Cell Proliferation

Since Tat is easily oxidized and photo and thermo-sensitive, the Tat protein was reconstituted in degassed PBS containing 0.1% bovine serum albumin (BSA) immediately prior to use, and the handling of the protein was performed in the dark and on ice. When carrying out the assay, oxidized Tat protein was included as a control. The oxidized Tat protein was prepared by exposing the active Tat protein to air and light for 24 hours. Cells were cultured in triplicate, at $2 \times 10^5$/well in 200 μl R-10 in the presence of active Tat or oxidized Tat proteins (5 μg/ml), or SIV p27 (2 μg/ml) (Advanced BioScience Laboratories, Inc., Kensington, Md.). Con A (5 μg/ml) and R-10 medium alone served as positive and negative controls, respectively. Following 5 days incubation at 37° C. in 5% $CO_2$, the cells were pulsed with [$^3$H]-thymidine (1 μCi per well) and further incubated overnight. Cells were harvested using a Mach IIM (Tomtech Inc.) cell harvester and counted on a Pharmacia (Wallac Inc.) beta-plate counter. Stimulation indices (SI) were calculated by dividing the mean counts per minute (cpm) with antigen by the mean cpm with medium alone.

Serological Responses

Anti-Ad5 neutralization titers were determined by micro-titer-neutralization assays on A549 cells as described previously (Chengalvala, et al., Vaccine 9:485-90, 1991), using serial two-fold dilutions of macaque sera. Endpoint titers were defined as the reciprocal of the last serum dilution at which an Ad5 cytopathic effect was not observed.

Serum antibodies to SIV Gag were assayed by enzyme-linked immunosorbent assay (ELISA) using 25 ng of SIV p27 per microtiter well and horse radish peroxidase-conjugated goat anti-mouse IgG (1:25000). All sera were initially tested at a 1:50 dilution and then titered to end point as needed. The binding titer was defined as the reciprocal of the serum dilution at which the absorbance of the test serum was twice that of the negative control serum diluted 1:50.

The presence of Tat-specific antibody was determined by an ELISA as previously described (Marinaro, et al., Vaccine 21:3972-81, 2003).

Statistical Methods

Data in this study were analyzed using standard univariate analysis of variance (anova), t-tests, non-parametric Wilcoxon tests and standard post hoc tests (e.g., Tukey's method) and simple descriptive and graphical techniques. All tests were two sided; probability values less than 0.05 were considered significant.

Results

In Vitro Expression of Wild Type and Mutant tat Genes in Adenovirus Recombinants Ad5hr-recombinants containing the full-length cDNA of the HIV-1 wild-type tat gene (Ad5hr-HIVtat-wt) or the Tat transdominant negative mutant (Ad5hr-HIVtat22) under the transcriptional control of a hybrid gene regulation unit, consisting of a human CMV promoter followed by the Ad5 tripartite leader sequence, were constructed as described in Materials and Methods. The Ad5hr vector was used to facilitate future efficacy studies in non-human primate models in which replication of the Ad-recombinant is desirable. As shown in FIG. 1, the levels of in vitro expression of the wild type and mutant tat genes were comparable following infection of human 293 cells with the Ad5hr-recombinants.

Antigen-Specific Cellular Immune Responses

To examine the immunogenicity of the candidate Ad5hr-HIVtat-wt and -HIVtat22 vaccines, ten mice each in groups I and II were immunized with an Ad5hr-recombinant encoding wild-type or mutant tat respectively. Because of previous reports concerning suppression of immune responses to other antigens co-administered with native Tat protein, we included immunization groups III-V, in which ten mice each received Ad5hr-SIVgag alone or together with Ad5hr-HIVtat-wt or Ad5hr-HIVtat22. A sixth control group received empty Ad5hr-ΔE3 vector only. Two additional groups (VII and VIII) were included to examine a possible immune modulating effect of prior immunity to wild-type or mutant Tat by administering first Ad5hr-HIVtat-wt or Ad5hr-HIVtat22 alone and 4 weeks later Ad5hr-SIVgag together with Ad5hr-HIVtat-wt or Ad5hr-HIVtat22. Immune responses were evaluated in these mice at week 6. Table I summarizes the various immunization groups.

Figure 2:
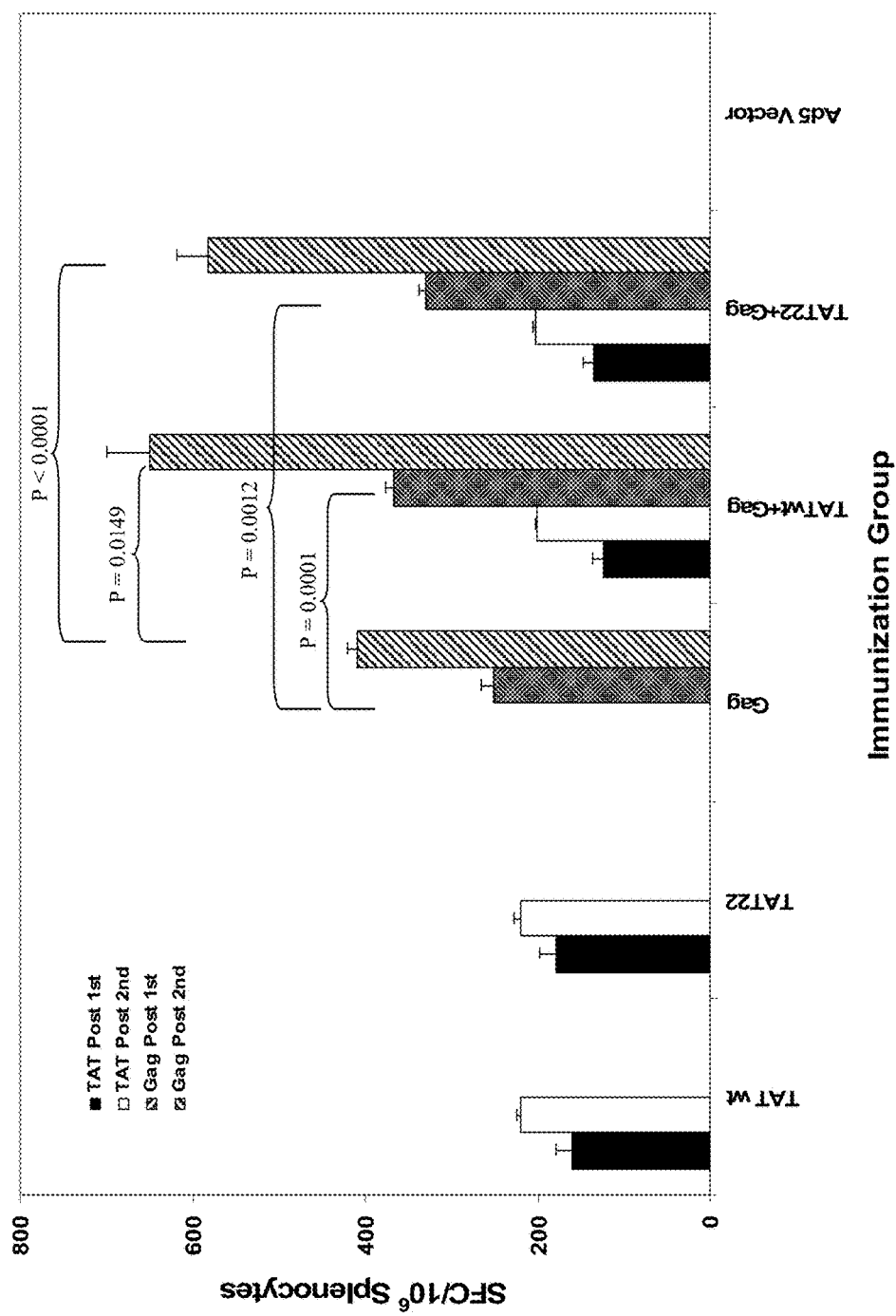

An IFN-γ ELISPOT assay was used to assess Tat- and Gag-specific cellular immune responses elicited by the Ad5hr-recombinant vaccines. Ad5hr-recombinants encoding Tat-wt and Tat22 were equally immunogenic, with no differences observed in the number of Tat-specific IFN-γ-secreting spot-forming cells (SFC) between groups I and II following either the first or second immunizations (FIG. 2). Similarly, the Tat-specific ELISPOT responses seen at both time points in Groups IV and V in which Ad5hr-SIVgag was co-administered were also equivalent. In all cases, except for group II mice immunized with Ad5hr-HIVtat22, a second immunization with the same Ad5hr-recombinant significantly boosted the Tat-specific cellular response ($p=0.028$, 0.071, 0.0031, and 0.023 for Groups I, II, IV, and V, respectively). A small but significant decrease in the number of IFN-γ-secreting cells in response to Tat peptides was seen in mice co-immunized with the Ad5hr-SIVgag recombinant and either Ad5hr-HIVtat-wt or -HIVtat22 following the second immunization (group I vs IV, $p=0.0096$; group II vs V, $p=0.0072$). The biological significance of these small decreases (20 mean SFC for tat-wt and 41 mean SFC for tat22) in the overall induced cellular response to Tat is considered minimal.

As previously seen in the macaque model (Zhao, et al., Vaccine 21:4002-35, 2003) the Ad5hr-SIVgag recombinant was also immunogenic in mice. A boosting effect of two sequential immunizations was seen in the Gag cellular immune response in all three groups that received this Ad5hr-recombinant ($p<0.0001$, $p=0.0094$, $p<0.0001$ for Groups III, IV, and V, respectively; FIG. 2). In contrast to the marginal decrease in cellular immune response to Tat seen upon co-administration of the Ad5hr-SIVgag recombinant, both the Ad5hr-HIVtat-wt and -HIVtat22 co-administrations significantly increased the number of Gag-specific IFN-γ-secreting cells following both the first and second immunizations (group III vs IV, $p=0.0001$ and $p=0.015$ post-first and -second; Group III vs V, $p=0.0012$ and $p<0.0001$ post-first and -second). The increases observed in the Gag-specific responses were 1.5-fold (116 mean SFC) and 1.3-fold (78 mean SFC) for mice immunized with the tat-wt recombinant and tat22 immunogens respectively at week 2, and 1.6-fold (240 mean SFC) and 1.4-fold (172 mean SFC) respectively at week 6. These results indicate that both wild-type and mutant Tat immunogens administered as Ad-recombinants can enhance the cellular immune response to a co-administered antigen. Although the Gag-specific cellular responses were slightly higher following one co-administration with Ad5hr-HIVtat-wt compared to Ad5hr-HIVtat22 (Group IV vs V, post-first, $p=0.014$), this difference disappeared following the second co-administrations (Group IV vs V, post-second, $p=0.20$). Thus, overall, both the wild-type and mutant Tat immunogens exerted a similar enhancing effect on the immune response of the co-administered SIV Gag immunogen.

In view of the strong enhancement of Gag-specific cellular immunity observed in the co-immunization groups, we looked for immune modulation of cellular immune responses to the Ad5hr-vector itself, by evaluating IFN-γ-secretion in response to the Ad5 fiber protein. No differences in ELISPOT responses to Ad5 fiber peptides were seen among any of the immunization groups (data not shown).

Figure 3:
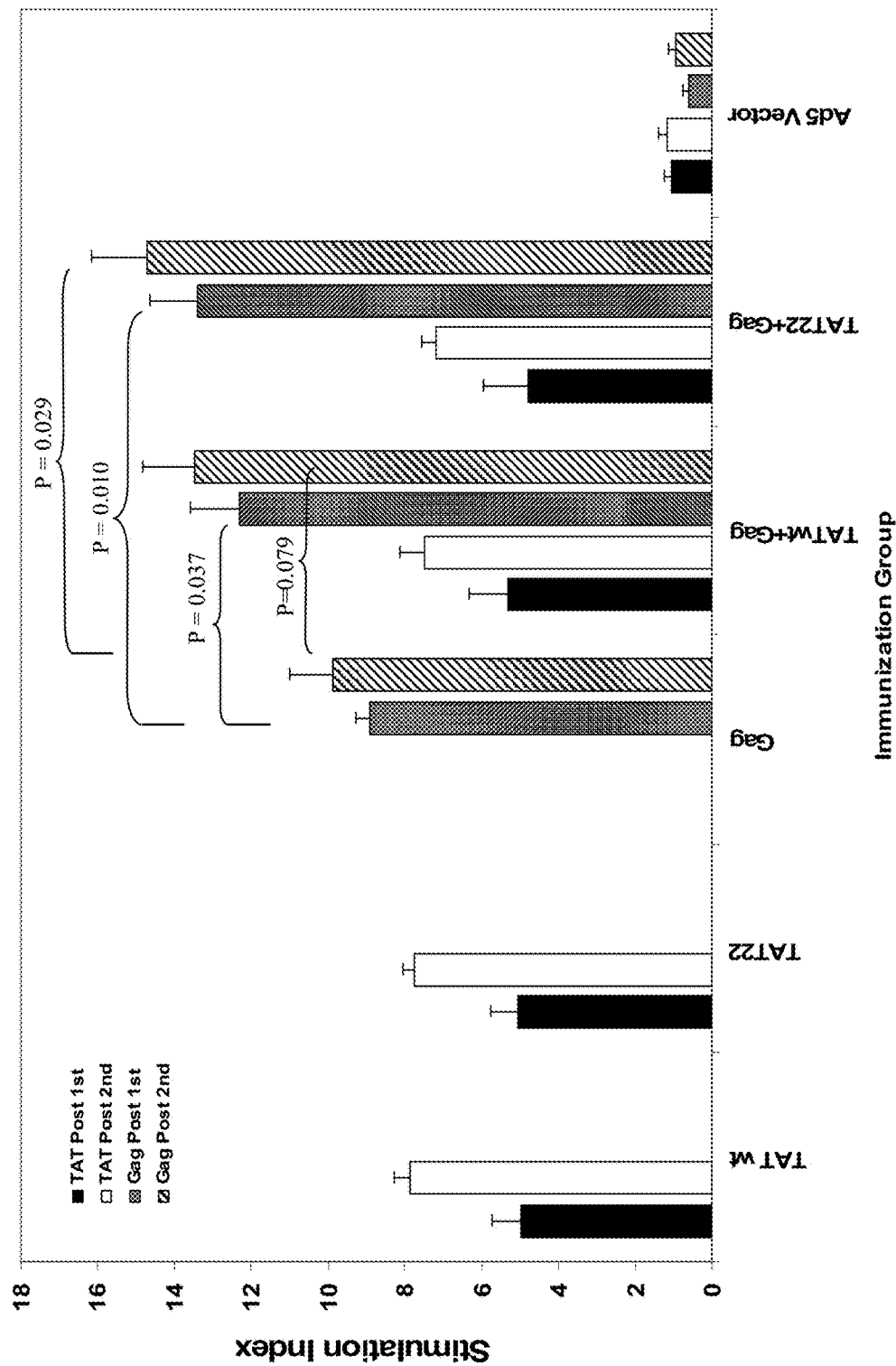
FIG. 3 provides exemplary data showing that the lymphoproliferative responses to HIV-1 Tat and enhanced responses to SIV Gag following co-administration of Ad5hr-ΔE3-HIVtat-wt or -HIVtat22 with Ad5hr-ΔE3-SIVgag recombinant immunizations. Freshly isolated splenocytes were incubated with HIV-1 native Tat or SIVmac p27 protein for 5 days. Following incubation, proliferative responses were measured by $^3$H-thymidine incorporation. Stimulation indices (SI) represent counts/minute in the presence of antigen divided by counts/minute in medium alone. Data are presented as mean SI±standard error of the mean.

T-cell proliferation assays were conducted to determine if the vaccine-induced cellular immune responses detected by ELISPOT assay were mirrored by responses to intact Tat protein and SIV p27. Proliferative responses to native and oxidized Tat protein were equivalent. Therefore, only results with the oxidized protein are shown. Similar to results obtained for IFN-γ secretion, no difference was observed in the ability of Ad5hr-HIVtat-wt or -HIVtat22 to elicit potent Tat-specific T cell proliferative responses. Mean SI in response to Tat protein (FIG. 3) were similar following each immunization regardless of whether mice received a single Ad-recombinant encoding native or mutant Tat, (Groups I and II) or were co-immunized with Ad5hr-SIVgag (Groups IV and V). A boosting of the Tat-proliferative response by a second recombinant administration was detected in immunization groups I and II ($p=0.0001$ and $0.0003$, respectively), and in groups IV and V that received the co-administered Ad5hr-SIVgag ($p=0.0030$ and $0.0002$, respectively). A single administration of Ad5hr-SIVgag recombinant was sufficient to elicit a potent Gag-specific proliferative response which was not significantly boosted by the second administration. We speculate that the immunization regimen was too compressed to allow optimal boosting of this induced immune response. The SI in response to p27 Gag was enhanced by co-administration of Ad5hr-recombinants encoding either tat-wt or tat22 (FIG. 3). Significant enhancement in the Gag proliferative response was seen by co-administration of the Tat-wt recombinant after the first administration (Group III vs IV; $p=0.037$) but not the second ($p=0.079$) and by co-administration of the Tat22 recombinant after both the first and second administrations (Group III vs V; $p=0.010$ and $0.029$ respectively).

Humoral Immune Responses

Having shown that both the Ad5hr-HIVtat-wt and -HIVtat$_{22}$ vaccines were immunogenic and able to elicit potent cellular immune responses, humoral immunity elicited by the vaccines was evaluated next. While enhanced cellular immunity to a co-administered antigen was demonstrated above, previous reports have shown suppression of antibody responses to a co-administered antigen in the presence of active Tat protein (Cohen, et al., Proc Natl Acad Sci USA 96:10842-7, 1999). Antibody titers induced following immunization with the Ad5hr-recombinants were relatively low overall. However, two weeks after the second Ad-recombinant immunizations, antibody responses to Tat and SIV p27 were detected in the appropriate immunization groups (Table 2). Anti-Tat titers in groups I and II and IV and V did not exhibit significant differences. Further, unlike the immune modulation seen in the cellular immune responses, no significant increase or decrease was observed in either anti-Tat or anti-Gag antibody titers upon co-administration of Ad5hr-HIVtat-wt or -HIVtat22 with Ad5hr-SIVgag compared to Ad5hr-SIVgag immunization alone. Overall, however, co-administration of Ad5hr-HIVtat-wt and Ad5hr-SIVgag induced greater anti-Gag titers than co-administration with the Ad-recombinant encoding HIVtat22 ($p=0.030$).

TABLE 2

Antibody responses to Tat and Gag post-second immunization.

| | | Antibody Titer (Geometric mean (range)) | |
|---|---|---|---|
| Group | Immunogen | Tat | Gag (p27) |
| I | Ad5hrΔE3-HIVtat-wt | 528 (50~3,200) | |
| II | Ad5hrΔE3-HIVtat22 | 44 (10~1,600) | |
| III | Ad5hrΔE3-SIVgag | | 2462 (10~18,500) |
| IV | Ad5hrΔE3-HIVtat-wt + Ad5hrΔE3-SIVgag | 106 (400~3,200) | 3724 (220~20,000)* |
| V | Ad5hrΔE3-HIVtat22 + Ad5hrΔE3-SIVgag | 69 (10~4000) | 88 (10~800)* |

Co-administration of Ad-recombinants encoding HIV Tat-wt or Tat22 and SIV Gag had no direct effect on elicitation of antibodies to either Tat or the SIV p27 Gag protein.
*Co-administration of Ad-recombinants encoding SIV Gag and HIV Tat-wt, elicited slightly higher anti-Gag antibody titers compared to co-administration of Ad-recombinants encoding SIV Gag and HIV Tat22 (p = 0.030).

Anti-Ad5 neutralizing titers were determined on mouse sera from all groups, and similar to results of ELISPOT assays for Ad5 fiber peptides, no significant differences were observed among the immunization groups.

Effect of Prior Tat Immunization on Elicitation of Immune Responses to Gag

To evaluate the effect of prior Tat immunization on elicitation of immune responses to Gag, two immunization groups were studied in which mice were first immunized with Ad5hr-HIVtat-wt (group VII) or Ad5hr-HIVtat$_{22}$ (groupVIII) alone, and then were co-administered the HIVtat-wt or HIVtat$_{22}$ recombinant together with Ad5hr-SIVgag at week 4. Following the co-administration, cellular and humoral immune responses to Gag were compared at week 6 to Gag responses in groups IV (Ad5hr-HIVtat-wt plus Ad5hr-SIVgag) and V (Ad5hr-HIVtat$_{22}$ plus Ad5hr-SIVgag) following a single co-administration (week 2). The results are shown in Table 3. There were no significant differences in Gag-specific IFN-γ secretion between groups with regard to prior Tat immunity. In addition, proliferative responses to p27 were not significantly decreased by prior immunization with Ad5hr-HIVtat-wt. However there was a marginally significant difference in the proliferative response to Gag following prior immunization with Ad5hr-HIVtat$_{22}$ (p=0.045). In general, two immunizations with the Ad5hr-SIVgag recombinant were needed for induction of a Gag-specific antibody response, so no prior effect of anti-Tat immunity on Gag antibody responses was observed.

TABLE 3

Effect of prior immunization with Ad-recombinants encoding Tat-WT or Tat22 on cellular response to co-administered Ad-recombinant encoding SIV Gag.

| Prior immunity to Tat | Gag-specific IFN-γ secreting cells (SFC/10$^6$ splenocytes) | T-cell proliferative response to p27 (Stimulation Index) |
|---|---|---|
| To Tat-WT | | |
| No | 367 ± 9 | 12.32 ± 1.25 |
| Yes | 378 ± 7 | 9.82 ± 0.5 |
| To Tat22 | | |
| No | 329 ± 7 | 13.4 ± 1.23* |
| Yes | 405 ± 37 | 10.23 ± 0.52* |

Mean values ∀ standard error of the mean reported.
*Marginally significant decrease in proliferative response to Gag following prior immunization with Ad-recombinant encoding Tat22 (p = 0.045).

Summary—Example 1

The present study illustrates the vaccine potential of a replicating Ad recombinant encoding HIV-1 Tat, a vaccine design that induces a more potent cellular immune response than would be expected for protein alone or DNA-based vaccines. We compared Ad-recombinants encoding both native Tat and a Tat mutant (tat22; Cys22 to Gly) lacking transactivation ability (Caputo, et al., Gene Ther 3:235-45, 1996). Intramuscular immunization of mice with plasmids encoding transdominant negative mutants of HIV-1 Tat including Tat22 was shown to elicit a humoral response to wild-type Tat comparable to that induced by inoculation of wild-type tat DNA (Caselli, et al., J Immunol 162:5631-38, 1999). Here we compared the immunogenicity of the two candidate vaccines and examined their effects on the immune response to a co-administered antigen, SIVgag.

In the present study we showed that both Tat-wt and the mutant Tat22, administered as Ad5hr-recombinants, are highly immunogenic in Balb/C mice. Cellular immune responses, including secretion of IFN-γ in response to Tat peptides and T-cell proliferative responses to both native and oxidized Tat protein, were readily detected after a single immunization and were efficiently boosted by a second immunization with the same recombinant. Immunization with vectored vaccines is typically aimed at eliciting cellular rather than humoral immune responses. In keeping with this, antibody responses to Tat required two immunizations for induction and overall were modest.

Not only were the Ad5hr-HIVtat-wt and -HIVtat22 recombinants immunogenic in mice, stimulating strong cellular responses to Tat, they also enhanced cellular immune responses to SIV Gag, co-administered as an Ad5hr-SIVgag recombinant. Enhancement of Gag-specific IFN-γ secretion and T-cell proliferation were both observed. This is in apparent contrast to previous reports showing immune suppressive effects of Tat (Li, et al., Science 268:429-31, 1995; Wu & Schlossman, Proc Natl Acad Sci USA 94:13832-7, 1997; Dockrell, et al., J Clin Invest 101:2394-405, 1998; Kolesnitchenko, et al., J Virol 71:9753-63, 1997; Cohen, et al., Proc Natl Acad Sci USA 96:10842-7, 1999), although there is an increasing body of evidence suggesting that the immunomodulatory activities of Tat are immunostimulating rather than immunosuppressive. In fact, recent data indicate that Tat in its native form selectively binds to and is taken up by DC in which it induces activation and maturation into mDC (Fanales-Belasio, et al. J Immunol 168:197-206, 2002). In particular, DC exposed to Tat upregulate key co-stimulatory molecules such as CD40, CD80, CD86, LFA-1, MHC Class I and II antigens, and produce inflammatory (TNF-α) and Th-1-polarizing (IL-12) cytokines and β-chemokines (RANTES, MIP-1 α and MIP-1 β). Of importance, in vitro responses to allo and recall antigens are also increased.

Further, Tat contains a cationic region, amino acids 48-60, identical in both the Tat-wt and Tat22 immunogens tested in Example 1, that increases expression of epitope/MHC class I complexes on the cell surface (Lindgren, et al., Trends Pharmacol Sci 21:99-103, 2000; Leifert, et al., Gene Ther 10:2067-73, 2003). However, it would not have influenced immunity to SIV Gag, administered as a separate Ad5hr-recombinant. Therefore, not to be bound by theory, the most likely explanation for the enhanced cellular immunity to Gag is an up-regulation of inflammatory and immunostimulating cytokines and chemokines attributable to Tat expression, leading to an overall cellular immune enhancement. Of note, recent data indicate that in B cells, both intracellular and extracellular Tat-wt and Tat22 modulate the composition of the catalytic domain of the proteasome, leading to increased generation and presentation of subdominant and cryptic epitopes of a co-administered antigen, thereby broadening the spectrum of epitopes recognized and the overall magnitude of the immune response (Gavioli, et al., *J Immunol* 173:3838-43, 2004).

Extracellular Tat has been shown to inhibit proliferation of naïve and memory B cells triggered via the B cell receptor (Lefevre, et al., *J Immunol* 163:1119-22, 1999). Elicitation of a potent anti-Tat antibody response appears to be a desireable feature for an effective HIV/AIDS vaccine, in order to inhibit early effects of extracellular Tat released from infected cells. To achieve this in combination with our Ad-recombinant priming strategy, boosting with Tat protein may be desirable in some embodiments. In fact, induction of high-titered antibodies to HIV and SIV envelopes by Ad5hr-recombinant priming followed by boosting with subunit proteins has been well documented (Lubeck, et al., *Nat Med* 3:651-8, 1997; Buge, et al., *J Virol* 71:8531-41, 1997). Similarly, priming of monkeys with DNA plasmids encoding Tat followed by boosting with Tat-protein together with ISCOM adjuvant has elicited strong anti-Tat responses (Mooij, et al., *J Virol* 78:3333-42, 2004).

Since the regulatory protein Tat plays a critical role in viral pathogenesis and infectivity, an AIDS vaccine desirably induces immune responses able to inhibit Tat function. Thus, in some embodiments, Tat will be included in a cocktail of HIV immunogens. We have previously shown significant protective efficacy against the highly pathogenic SIVmac251 strain, achieved by priming with multi-genic Ad5hr-SIV recombinants and boosting with envelope subunits (Patterson, et al. *J Virol* 78:2212-21, 2004). The present results indicate that Tat can be incorporated into a similar vaccine strategy without inhibiting cellular immune responses elicited by other Ad-recombinants. Further, boosting with Tat protein may provide additional high-titered antibodies to inhibit early Tat functions, leading to better control of viral exposures.

Example 2. Development of Anti-Tat Antibodies in Rhesus and Cynomolgus Monkeys by Priming with Ad-HIVtat Recombinant and Boosting with Tat Protein This example demonstrates that a replication competent adenovirus of the invention is immunogenic in monkeys.

Figure 4:
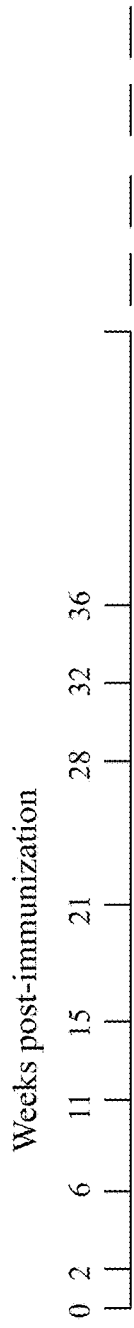
FIG. 4 shows an exemplary protocol for administering Ad5hr-HIVtat$_{WT}$ to elicit an antibody response in monkeys.
Figure 4:
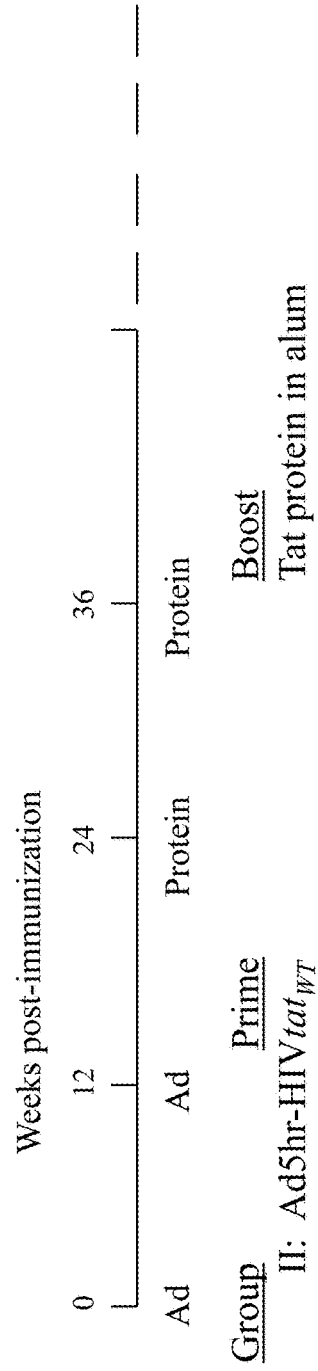

The immunization protocol is shown in FIG. 4. Macaques in Group I were immunized 8 times with Tat protein in alum adjuvant; once with Tat formulated in ISCOM. Macaques in Group II were immunized twice with Ad-HIVtat$_{WT}$ (first intranasally, 5×10$^8$ pfu; and second intratracheally, same dose) and boosted twice with Tat protein in alum. The same protocol was used in both cynomolgus monkeys and rhesus macaques.

Results in cynomolgus monkeys: Similar anti-Tat antibody titers were achieved at the end of these immunization regimens by week 38 post-immunization, indicating the Ad-Tat recombinant regimen reduced the number of immunizations.
  Group I: Titer=22,200
  Group II: Titer=12,066
Results in Rhesus macaques: Similar results as above:
  Group I: Titer=1650
  Group II: Titer=1550

These results show that the Ad-tat constructs were immunogenic in primates. In addition, they had the ability to decrease the number of immunizations to needed to elicit a strong antibody response.

Example 3. Immunogenicity of Ad-HIVnef and Ad-HIVnef Mutant Replication Competent Ad5 Vaccines in Primates In Vivo Immunogenicity of Ad-HIVnef and Ad-HIV Ad-HIVnef mutant vaccines was examined in vivo in primates. It was previously shown that deletion of the amino terminal 19 amino acids of Nef, including the myristoylation site, prevents Nef-induced down-modulation of both CD4 and MHC-1 (Peng & Robert-Guroff, *Immunology Letters* 78:195-200, 2001). It was therefore predicted that the mutated nef construct would elicit more potent cellular immune responses. This was verified in an experiment employing chimpanzees, which is detailed below. These experiments used replication competent Ad5 and Ad7 HIV-nef vectors and demonstrate that such vectors are immunogenic in vivo. The permissive chimpanzee system was selected, as it is an animal model that is highly homologus to humans.

Methods
Ad-HIVnef Constructs pT7consnefhis6, which contains a consensus HIV-1 nef gene based on 54 HIV-1 patient isolates (Shugars, et al. *J. Virol* 67:4639-4650, 1993), was from AIDS Research and Reference Reagent Program, NIAID, NIH. Plasmids pBRAd5ΔE3, pBRAd7ΔE3 and pAd7tpl7-18RD were obtained from Wyeth-Lederle Vaccines under a Cooperative Research and Development Agreement. pAdenoVator-CMV5 (pAV-CMV5) was purchased from QBiogene (Irvine, Calif.). The plasmid pBRAd5ΔE3 contains the right arm of the Ad5 genome from 59.5 to 100 map units (mu) in which the E3 region from 78.8 to 85.7 mu is deleted. The plasmid pBRAd7ΔE3 contains the right arm of the Ad7 genome from 68 to 100 map units (mu) in which the E3 region from 80-88 mu is deleted.

Replication competent Ad5-HIVnef$_{WT}$ and HIVnef$_{NM}$ were constructed as follows. First, HIVnef$_{WT}$ was amplified using PCR primers Nef (WK) p1: 5'-GCGGCCGCGTTAAC ACCATGGGTGGCAAGTG GTCAAAACGT-3' (SEQ ID NO:11) and Ad nef primer A: 5'-TTATCAGCAGTCTTTG-TAGTACTCCG-3' (SEQ ID NO:12). HIVnef$_{NM}$ was amplified using: Nef (184) primer 6: 5'-GCGGCCGCGT-TAACACCATGAGGCGAGCTGAG CCAGCAGCAGA-3'(SEQ ID NO:13) and the Ad nef primer A. Both amplified nef gene fragments were inserted separately into pAV-CMV5 between sites PmeI and BamHI, resulting in pCM-VSnef-1 (containing HIVnef$_{WT}$) or pCMVSnef-2 (containing HIVnef$_{NM}$). Secondly, the expression cassette of CMV-Ad5tpl-nef$_{WT}$ (or nef$_{NAT}$)-polyA of pCMVSnef-1 or pCMVSnef-2 was amplified using the primer pair of CMV5 p1 (5'-CCTCTAGTTATA GTAATCAATTACGGGGT-CATT-3') (SEQ ID NO:3) and CMV5 p2 (5'-CCTCTA-GATC TCCGAGGGATCTCGACCAAAT-3') (SEQ ID NO:10), and then inserted into the Xba1 site at 78.8 mu of pBRAd5ΔE3, resulting pBRAd5ΔE3HIVnef$_{WT}$ or pBRAd5ΔE3HIVnef$_{NM}$. Ad5-HIVnef$_{WT}$ and Ad5-HIVnef$_{NM}$ recombinants were generated by homologous recombination between Ad5 viral DNA (1-75 mu) and pBRAd5ΔE3HIVnef or pBRAd5ΔE3HIVnef$_{NM}$ as described previously (Zhao, et al. *Vaccine* 214022-4035, 2003).

Ad7-recombinants carrying HIVnef$_{WT}$ and HIVnef$_{NM}$ were constructed as follows. First, using pCMVSnef-1 or pCMVSnef-2 as a template, the CMV promoter, HIVnef$_{WT}$ or HIVnef$_{NM}$ and polyA were amplified separately using PCR with three pairs of primers: CMV5p1 and CMVA7tpl7p2: 5'-GCGATCCGGAAGACGACAGTG-GATCTGACGGTTC ACTA-3' (SEQ ID NO:14); Ad7tplNeflp1: 5'-CAGTCGCAATCGCAAGGTTT AAACACCATGGGTGGCAAGTGGT-3' (SEQ ID NO:15); or Ad7tplnef2p1 (for HIVnef$_{NM}$): 5'-CAGTCGCAATCG-CAAGGTTTAAACACCATGAGGCGAGCTGAG-3' (SEQ ID NO:16) and CMV5p2. Secondly, using pAd7tpl7-18RD as a template, the tpl of the Ad7 serotype was amplified using a pair of primers CMVA7tplp1: 5'-TAGT-GAACCGTCA GATCCACTGTCTTCCGGATCGC-3' (SEQ ID NO:17); and Ad7tplNef-1p2: 5'-ACCA CTTGC-CACCCATGGTGTTTAAACCTTGCGATTGCGACTG-3' (SEQ ID NO:18); or Ad7tplNef-2p2 (for HIVnef$_{NM}$): 5'-CTCAGCTCGCCTCATGGTGTTTAAACCTTGC GAT-TGCGACTG-3' (SEQ ID NO:19). Finally, an expression cassette of CMV-Ad7tpl-nef$_{WT}$ (or nef$_{NM}$)-polyA was assembled by combining the above PCR products as template and amplified using the primer pair CMV5p1 and CMV5p2. The amplified expression cassette was then inserted into the Xba1 site at 80 mu of pBRAd7ΔE3. The correct gene orientation and sequence of both pBRAd7ΔE3HIVnef$_{WT}$ and pBRAd7ΔE3HIVnef$_{NM}$ were confirmed by DNA sequencing. Ad7-HIVnef$_{WT}$ and Ad7-HIVnef$_{NM}$ recombinants were generated by homologous recombination between Ad7 viral DNA (1-87 mu) and pBRAd7ΔE3HIVnef$_{WT}$ or pBRAd7ΔE3HIVnef$_{NM}$ as described above.

Expression of the Nef proteins of the Ad5- or Ad7-HIVnef$_{WT}$ or Ad5- or Ad7-HIVnef$_{NM}$ recombinants was evaluated in human 293 and A549 cells using Western blot. The 293 cells or A549 cells were infected at an MOI of 10 with Ad5- or Ad7-HIVnef$_{WT}$ or Ad5- or Adz-HIVnef$_{NM}$ recombinants and Ad5ΔE3 virus or Ad7ΔE3 virus as a negative control. When 90% of the cells exhibited a cytopathic effect, cell lysates were prepared with radioimmunoprecipitation assay buffer (50 mM Tris-HCl, pH 8.0, containing 150 mM NaCl, 1% polyethoxyethanol (Sigma, St. Louis, Mo.), 0.5% sodium deoxycholate, 0.1% sodium dodecyl sulfate (SDS), and 1 mM phenylmethylsulfonyl fluoride), separated on an SDS-polyacrylamide gradient gel of 4-20% (Bio-Rad), and then transferred onto a nitrocellulose membrane (Bio-Rad). Nef expression was determined by incubating the membrane with anti-HIV-1 Nef antiserum (AIDS Research and Reference Reagent Program, NIAID, NIH) and subsequently visualizing bands using the ECL Western blotting detection reagent (Amersham Pharmacia Biotech, Piscataway, N.J.), as described by the manufacturer.

Immunization Protocol

Four chimpanzees were used for the study. Three males and one female, ranging in age from 8 to 22 years and possessing comparable Ad5 and Ad7 neutralizing antibody titers were selected for study and placed into two immunization groups (Table 4). At week 0, the animals were immunized intranasally with $10^7$ plaque forming units of replicating Ad-recombinants encoding wild-type HIV Nef or mutated HIV Nef, lacking amino acids 1-19 including the myristoylation site (Ad5-HIVnef$_{WT}$ or Ad5-HIVnef$_{NM}$, respectively). A booster using a similar intranasal dose of Ad7-HIVnef$_{WT}$ or Ad7-HIVnef$_{NM}$, as indicated, was administered at week 12.

TABLE 4

Chimpanzee Immunization Schedule.
Pre-inoculation Ad5 or Ad7
neutralizing antibody titer*

| Chimpanzee | Age | Sex | Ad5 | Ad7 | Week 0 | Week 12 |
|---|---|---|---|---|---|---|
| 329 | 15 | M | 4 | 4 | Ad5-HIVnef$_{WT}$ | Ad7-HIVnef$_{WT}$ |
| 380 | 11 | M | 4 | 4 | Ad5-HIVnef$_{WT}$ | Ad7-HIVnef$_{WT}$ |
| 202 | 22 | M | 8 | <2 | Ad5-HIVnefNM | Ad7-HIVnef$_{NM}$ |
| 424 | 8 | F | 4 | 4 | Ad5-HIVnefNM | Ad7-HIVnef$_{NM}$ |

*Reciprocal neutralizing antibody titers are shown. Ad-HIVnef recombinants were administered intranasally in 1 ml PBS, 0.5 ml per nostril, with a final dose of 1 × 10⁷ pfu.

Results

Elicitation of cellular immune responses was monitored periodically by T-cell proliferation assay and ELISPOT assay over the course of 40 weeks. Higher responses were observed in the chimpanzees immunized with the Ad-recombinant encoding mutated Nef. These results show that both replicating Ad-recombinants are immunogenic, but that higher Nef-specific cellular immune responses are induced by the recombinant encoding the mutated nef. The results are shown in greater detail below.

Cellular Immune Responses

HIV Nef-specific interferon-gamma (IFN-γ)-secreting cells were evaluated using human IFN-γ ELISPOT kits (BD Biosciences, San Diego, Calif.). HIV Nef peptides matched to the consensus sequence were provided as forty-eight 15mers with an overlap of 11 amino acids (Advanced BioScience Laboratories, Inc. (ABL), Kensington, Md.). The peptides were pooled and used at a final concentration of 2 µg/ml of each peptide to stimulate PBMC serially diluted from $4 \times 10^5$ to $0.5 \times 10^5$ cells for 30 hours in 100 µl of RPMI 1640 medium containing 10% human AB serum and 2 mM L-glutamine (R10) per well. Concanavalin A (Sigma) at 5 µg/ml, R10, and R10 containing 0.3% dimethyl sulfoxide were positive and negative controls. Spots were counted with a KS ELISPOT reader (Zeiss, Inc.) Results are reported following subtraction of negative control spots.

T-cell proliferative responses were assessed by first culturing PBMC ($10^5$ cells/well) in the presence of 1 µg HIV Nef (ABL) for 6 days in triplicate in 200 µl of R10. The cells were then pulsed overnight with [$^3$H]thymidine (1 µCi/well), harvested and counted. Concanavalin A (5 µg/ml) and R10 were positive and negative controls respectively. Results are reported as stimulation indices (mean counts per minute with Nef antigen divided by mean counts per minute with R10).

Intracellular Cytokine Staining of Memory Cells

HIV Nef-specific central and effector memory cells were quantified by flow-cytometry using viably frozen PBMC. The cells were thawed and cultured overnight at 37° C. in RPMI supplemented with 10% heat-inactivated fetal bovine serum, 100 units/ml penicillin, 100 µg/ml streptomycin and 2 mM L-glutamine (complete RPMI) plus recombinant IL-2 (20 units/ml). Following this incubation, cells were counted, resuspended at $2 \times 10^6$ cells/ml in complete RPMI plus recombinant IL-2 (20 units/ml) and 2 ml of cell suspension was aliquoted into each of three flasks. Cells were either left unstimulated or were stimulated with SEB (200 ng/ml) or Nef peptides (2 µg/ml each) at 37° C., 5% CO2. Both unstimulated and stimulated cells were co-stimulated with CD28 (1 µg/ml) and CD49d (1 µg/ml). Cells were stimulated with Nef peptide for 18 hr and Golgi Plug (1 µg/ml) was added for the last 5 hr of stimulation. Alternatively, cells were stimulated with SEB in the presence of Golgi Plug for 5 hr. Following stimulation, cells were collected by centrifugation at 1500 RPM for 5 min at 4° C. and washed with 1×PBS.

Cells were then stained using mouse anti-human FITC-conjugated anti-CD45RA and PE-Cy7-conjugated anti-CD8 (BD BioSciences). Cells were also stained for the presence of the surface marker, CCR7, in a two-step process using purified anti-CCR7 (IgM isotype) and anti-IgM-PE antibodies (BD BioSciences). Intracellular cytokine staining was then carried out as per the manufacturer's protocol using mouse anti-human APC-conjugated TNF-α, IFN-γ, or IL-2 monoclonal antibodies followed by cytometry analysis. Gating was performed on CD45RA-CD8+(CD8+ memory T cells), CD45RA-CD8– (CD4+ memory T cells). Following this gating, CCR7+(central memory) and CCR7– (effector memory) cells that were positive for Th1 (TNF-α, IFN-γ, IL-2) cytokines were measured. Cells were acquired using a FACScalibur cytometer and analysis was performed using Cell Quest software (BD BioSciences).

Statistical Analysis

Data were analyzed using repeated measures analysis of variance (anova), linear hierarchical mixed-effects models, generalized least squares regression models, simple and advanced graphical techniques, AUC analyses, and post hoc tests (Littell et al., *SAS System for Mixed Models*, SAS Institute, Inc, 1996; Milliken et al., *Analysis of Messy Data, Volume 1: Designed Experiments*, Chapman and Hall, New York, 1992; Pinheiro et al., *Mixed-Effects Models in S and S-Plus*, Springer-Verlag, New York, 2000). Mixed-effects and generalized least squares models permit increased flexibility in modeling within-animal correlation in responses over time. In this study, alternative within-chimp correlation structures (e.g., autoregressive order 1 autocorrelation) and covariance structures were routinely fit to data; assumptions regarding homogeneity of variance and covariance were examined and assessed in the determination of the best-fitting models. All tests were two-sided; probability values less than 0.05 were considered significant.

Results

ELISPOT Responses

Figure 5:
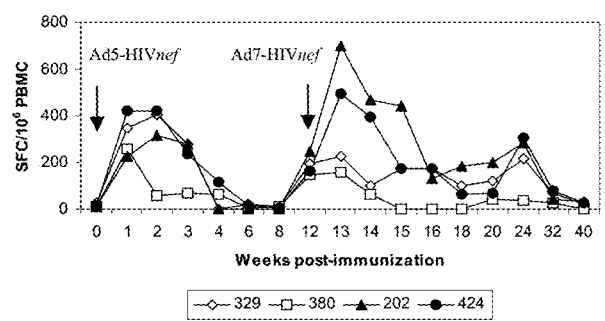
FIG. 5 provides exemplary data showing quantification by ELISPOT of IFN-γ-secreting PBMC in response to stimulation with Nef peptides.

Secretion of IFN-γ in response to stimulation of chimpanzee PBMC by overlapping HIV Nef peptides was evaluated by ELISPOT analysis. As shown in FIG. 5, the immunization regimen elicited Nef-specific cellular immune responses after both the Ad5-HIVnef$_{WT}$ and -HIVnef$_{NM}$ immunizations at week 0 in all four chimpanzees, although numbers of IFN-γ-secreting cells fell to baseline by week 6 post-immunization. The mean peak number of IFN-γ-secreting cells per million PBMC for chimpanzees immunized with Ad5-HIVnef$_{WT}$ was 333 and for chimpanzees immunized with Ad5-HIVnef$_{NM}$ was 368. Following immunization with the Ad7-HIVnef recombinants at week 12, responses of chimpanzees immunized with the Ad-HIV recombinants encoding nef$_{NM}$ (#202 and #424) were boosted, and exhibited an elevated mean peak number of IFN-γ-secreting cells (598 SFC/106 PBMC) compared to chimpanzees that received the recombinants encoding nef$_{WT}$ (#329 and #380). The response of these latter chimpanzees was not boosted at all (mean peak SFC/106 PBMC of 193). Analysis of ELISPOT responses over weeks 13-24 confirmed enhanced cellular immunity in the chimpanzees immunized with the Ad-HIVnef$_{NM}$ recombinants with a statistically significant difference at the p=0.0017 level. The overall response in chimpanzees #202 and #424 was also more prolonged following the second immunization than after the first, indicative of the boosting effect. Of the chimpanzees immunized with the Ad-HIVnef$_{WT}$ recombinants, only chimpanzee #329 exhibited sustained numbers of IFN-γ-secreting cells out to 24 weeks.

T-Cell Proliferative Responses

Figure 6:
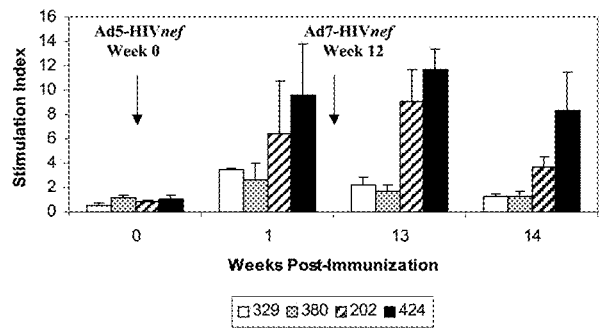
FIG. 6 provides exemplary data showing T-cell proliferative response to Nef.

Better induction of Nef-specific T cell proliferation was also seen following immunization with the Ad recombinants encoding nef$_{NM}$ compared to nef$_{WT}$. Following the first Ad5-HIVnef immunizations, chimpanzees immunized with the recombinant encoding HIVnef$_{WT}$ exhibited a mean stimulation index (SI) of 3.1, while for those immunized with Ad5-HIVnefNM, the mean SI was 8.0. Similarly to the ELISPOT responses, following the booster immunization with the Ad7-HIVnef recombinants, the proliferative responses of chimpanzees immunized with the recombinants encoding HIVnef$_{WT}$ were not boosted (mean SI of 2.0) while those of chimpanzees immunized with the recombinant encoding HIVnef$_{NM}$ exhibited slightly elevated SI (mean of 10.4). The responses of the individual chimpanzees are illustrated in FIG. 6. The increased proliferative responses in chimpanzees #202 and #424 after both the first Ad5-HIVnef$_{NM}$ immunization (week 1) and second Ad7-HIVnef$_{NM}$ immunization (weeks 13 and 14) were significant at the p=0.0012 level.

T Cell Memory Responses

Figure 7A:
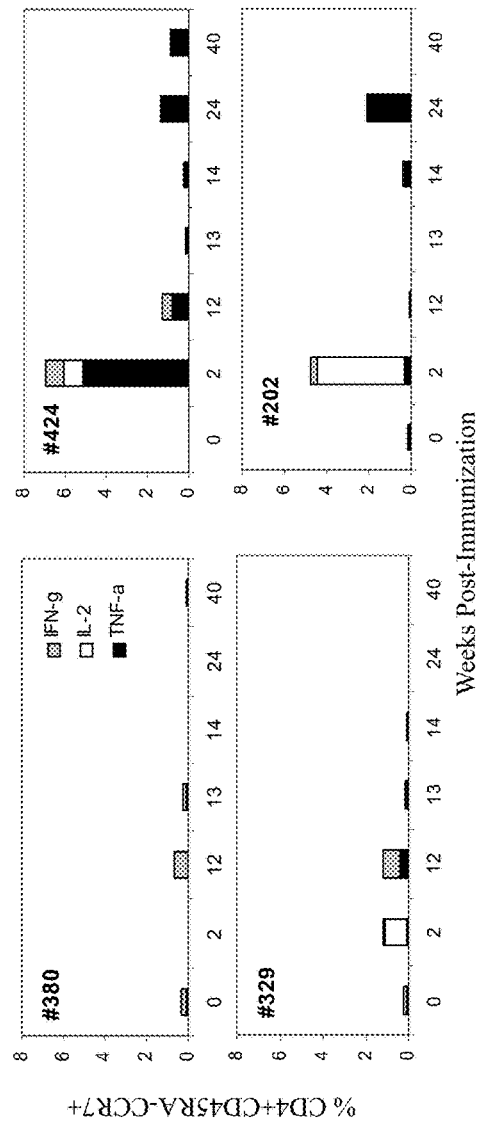
FIGS. 7A and 7B provide data from an exemplary analysis of Nef-specific central and effector CD4 memory T cells.
Figure 7B:
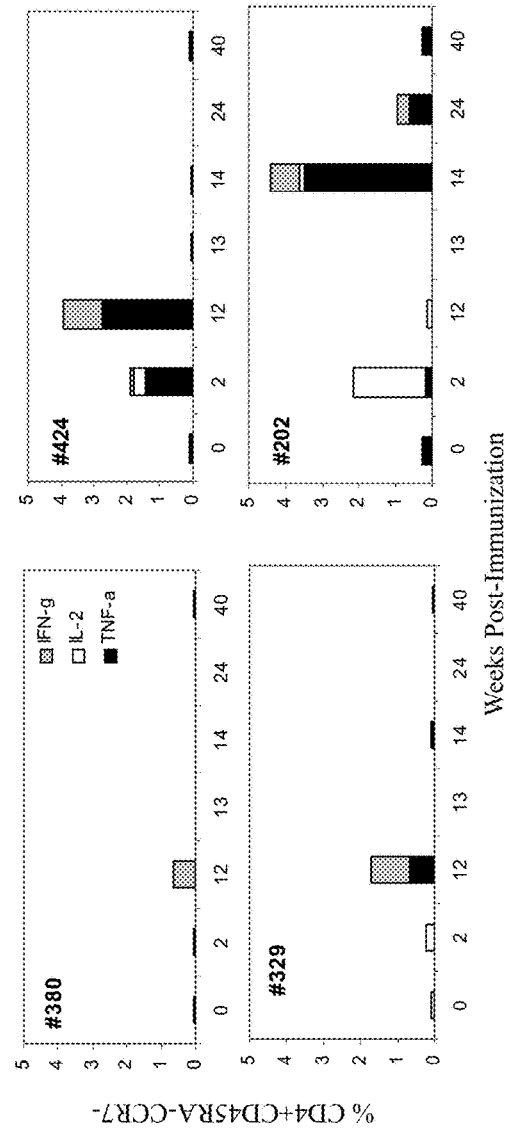

An important component of a successful vaccine for HIV/AIDS is the ability to elicit memory T cells, able to respond to specific viral antigens long after vaccination. The influence of the deletion of the Nef myristoylation site on induction of Nef-specific CD4 and CD8 central ($T_{CM}$) and/or effector ($T_{EM}$) memory T cells was therefore evaluated. While central and effector memory T cells are heterogeneous and can exhibit a spectrum of distinct phenotypes and functional capacities (e.g., Sallusto, et al., *Annu. Rev. Immunol.* 22:745-763, 2004), expression of CCR7, a chemokine receptor that controls homing to secondary lymphoid organs, can readily divide CD45RA– cells into the two distinct $T_{CM}$ and $T_{EM}$ populations (Sallusto, et al., *Nature* 401:708-712, 1999). Following stimulation with Nef peptides, CD45RA– CD4+ and CD8+ T cells, positive ($T_{CM}$) or negative ($T_{EM}$) for CCR7 expression, were analyzed for secretion of IFN-γ, IL-2, and TNF-α. Analysis of CD4 memory T cells is presented in FIG. 7. De Rosa et al (De Rosa et al., *J. Immunol.* 173:5372-5380, 2004) have shown that meaningful quantification of cellular immune responses requires measurement of more than a single cytokine. In fact, they reported that secretion of IFN-γ is often a sub-dominant response. To better evaluate the overall immune response to Nef, we measured percentages of cells secreting each of the three cytokines and assembled them together graphically, although the individual cytokine profiles are also shown. The combined totals of responses were used for statistical analysis. TNF-α appeared to be the most prevalent cytokine secreted in response to Nef stimulation of PBMC, although small amounts of IFN-γ and IL-2 were also elicited. The Ad recombinants encoding HIVnef$_{NM}$ elicited significantly greater percentages of CD4+ central memory T cells compared to the Ad-HIVnef$_{WT}$ recombinants (FIG. 7A). The enhanced response was seen both following the first Ad recombinant immunization (weeks 0-12; p=0.0133) with the difference due primarily to elevated responses at week 2, and following the second Ad recombinant immunization (weeks 13-40; p=0.0051) with the difference due primarily to elevated responses at week 24. The chimpanzees immunized with the Ad-HIVnef$_{NM}$ recombinants tended to exhibit higher percentages of Nef-specific CD4+ effector memory T cells (FIG. 7B), but statistically significant differences were not observed.

Figure 8A:
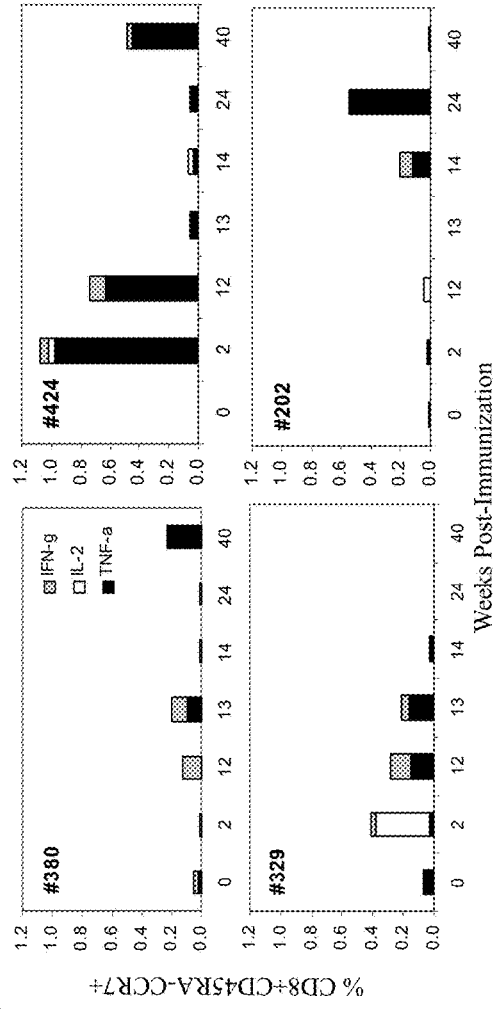
FIG. 8A, Nef-specific CD8 central memory cells.

Nef-specific memory CD8+ T cell responses are shown in FIG. 8. Again, all three cytokines are plotted together. Nef-specific CD8+ central memory T cells were clearly elicited by Ad recombinants encoding both HIVnef$_{WT}$ and HIVnef$_{NM}$ (FIG. 8A), although the overall level of percent positive cells was lower than that attained by the CD4+ central memory T cells elicited by the Ad-HIVnef$_{NM}$ recombinants in chimpanzees #424 and #202 (FIG. 7A). While elevated responses were exhibited by PBMC from chimpanzees #424 and #202, they were not significantly different in comparison to responses seen in chimpanzees #380 and #329.

Figure 8B:
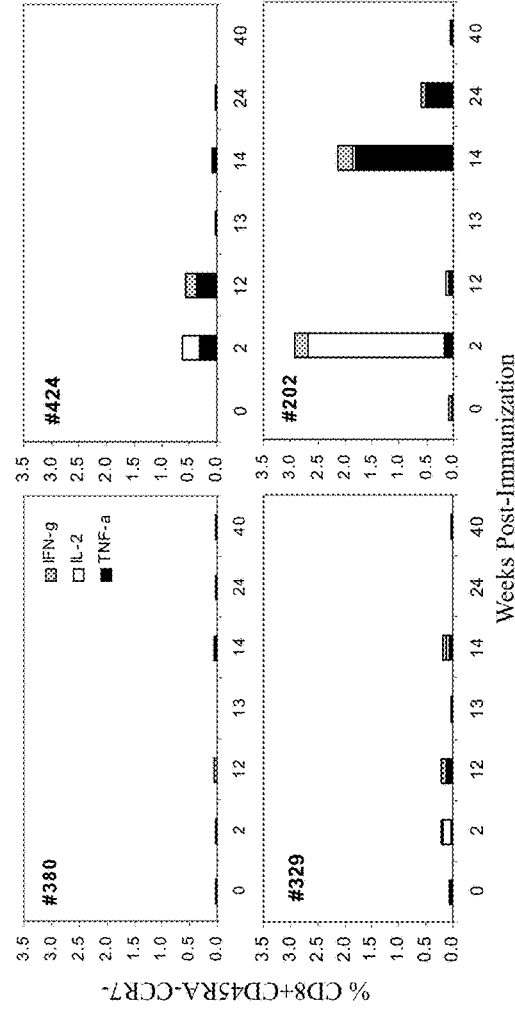
FIG. 8B, Nef-specific CD8 effector memory cells

Similarly, the chimpanzees immunized with Ad-HIVnef$_{NM}$ exhibited the highest percentages of CD8+ effector memory T cells over the immunization course (FIG. 8B). A large variability was seen in the kinetics of immune response of the two chimpanzees, and again, significant differences were not observed in comparison to chimpanzees immunized with the Ad recombinants encoding HIVnef$_{WT}$.

These results show that replication competent Ad-HIV recombinants encoding non-myristoylated nef elicited enhanced Nef-specific cellular immune responses compared to Ad-HIV recombinants encoding wild-type nef. Significantly elevated immune responses were exhibited by the chimpanzees immunized with the Ad5- and Ad7-HIVnef$_{NM}$ recombinants as determined by ELISPOT and T-cell proliferative assays. Of interest was the fact that Nef-specific cellular immune responses were not boosted following the second immunization at week 12 in chimpanzees that received the Ad-HIVnef$_{WT}$ recombinants, whereas, boosting was evident in the responses of chimpanzees immunized with the Ad-HIVnef$_{NM}$ recombinants. This observation can perhaps be explained by the loss of CD4 help in the chimpanzees immunized with the HIVnef$_{WT}$ recombinants, resulting from Nef-mediated down-modulation of MHC-II and/or CD4 together with increased expression on the cell surface of the invariant chain. These effects that require the Nef myristoylation site would have been diminished or abrogated in the chimpanzees immunized with the Ad-HIVnef$_{NM}$ recombinants. While memory CD8+ T cells can be generated in the absence of CD4 help, the quality of these cells is dependent on CD4 help (Kaech et al., *Science* 300: 263-265, 2003). Several studies have shown that while memory CD8 cells can be generated in the absence of CD4 help, they exhibit very poor recall responses and little proliferative capacity upon encountering antigen a second time (Bourgeois et al., *Science* 297:2060-2063, 2002; Janssen et al., *Nature* 421:852-856, 2003; Shedlock et al., *Science* 300: 337-339, 2003; Sun et al., *Science* 300: 339-342, 2003). With regard to the study here, lack of CD4 help resulting from down-mudulation of MHC-II and/or CD4 would have allowed a primary immune response, but an impaired recall response. This is clearly seen in the ELISPOT results, where similar levels of IFN-γ-secreting cells were exhibited by animals in both immunization groups after the first immunization, but following the second immunization, elevated responses were seen only in the chimpanzees immunized with the Ad-HIVnef$_{NM}$ recombinants. With regard to the T-cell proliferative responses to Nef protein, strong proliferative responses were observed following each immunization with the Ad-HIVnef$_{NM}$ recombinants, but only low level SI were observed in the Ad-HIVnef$_{WT}$ group, after both the first and second immunizations. In this case, down-regulation of MHC-II and CD4 likely affected the primary as well as the recall response.

To evaluate memory T cell responses, we separately measured secretion of three cytokines, IFN-γ, IL-2, and TNF-α, in response to stimulation with Nef peptides, but used the sum of the three Th1 cytokines for statistical analysis. Wille-Reece et al (Wille-Reece et al., *Proc. Natl. Acad. Sci. USA.*, 102:15190-15194, 2005) have reported that these three cytokines effectively measure the quality of the cellular immune response, as IL-2 is important for sustaining memory and both IFN-γ and TNF-α are important for effector functioning. In line with this observation, in many, but not all cases, secretion of IL-2 was observed after the initial Ad-HIV recombinant immunization whereas TNF-α was the predominant cytokine secreted following the second immunization. More frequent sampling of chimpanzee PBMC would have given a more comprehensive profile of cytokine secretion in conjunction with memory cell development. In general, the Ad-HIVnef$_{WT}$ recombinants elicited low level CD4 and CD8 central and effector memory T cells, while higher responses were observed in the chimpanzees immunized with the Ad-HIVnef$_{NM}$ recombinants. A statistically significant enhancement was only obtained for the Nef-specific CD4 central memory T cells, however, in part attributable to small group sizes (2 animals/group) and different kinetics of immune responses among the chimpanzees.

Nef expressed on the surface of cells might be a target for cell lysis by Nef-specific antibodies mediating ADCC. Vectored vaccines are primarily intended to elicit cellular rather than humoral responses; accordingly, these studies focus on cellular immunity. In this regard, following the two Ad-HIVnef recombinant immunizations, peak anti-Nef antibody titers elicited in the chimpanzees were very low. The titers were as follows: for #329, 75; #380, 285; #202, 230; and #424, <50. As with elicitation of anti-HIV envelope antibodies, development of high-titered anti-Nef antibodies will require boosting with Nef protein.

HIV nef has been identified as an optimal antigen for vaccine design based on its potent induction of cellular immune responses for a protein of its size, its relatively conserved sequence, and its overall immunogenicity (Betts et al., *DNA Cell Biol.* 21: 665-670, 2002). Studies of HIV-infected people have confirmed that it is well recognized by the immune system, as reflected by potent immune responses early in infection, (Lichterfeld et al., *AIDS* 18: 1383-1392, 2004) and by broad recognition in people of multiple ethnicities (Frahm et al., *J. Virol.* 78: 2187-2200, 2004). Nef-specific cellular immune responses have even been seen in individuals highly exposed to HIV infection but persistently seronegative (Rowland et al., *Nat Med.* 1: 59-64, 1995 Erratum: *Nat Med,* 1:598, 1995), suggesting both potent immunogenicity and a role in protective efficacy.

Pre-clinical vaccine studies in non-human primates have shown that nef-based vaccines are immunogenic (Patterson et al., *DNA Cell Biol.* 21: 627-635, 2002; Hel et al., *DNA Cell Biol.* 21: 619-626, 2002), and can contribute to protective efficacy in macaques against SIV and SHIV challenge exposures (Patterson et al., *J. Virol.* 78:2212-2221, 2004; Erfle et al., *Microbes Infect. In press,* 2005; Voss et al., *J. Virol.* 77:1049-1058, 2003). As immune therapeutic agents, HIV nef vaccines have also been shown to elicit new cellular immune responses in HIV infected individuals (Cosma et al., *Vaccine* 22: 21-29, 2003; Harrer et al., *Antivir. Ther.* 10: 285-300, 2005). Taken together, studies to date indicate that nef is an attractive target for vaccine design. The enhanced cellular immune responses exhibited here in response to immunization with Ad-recombinants encoding non-myristoylated nef indicate a significant advantage over immunizations with Ad-HIVnef$_{WT}$ recombinants.

The above examples are provided by way of illustration only and not by way of limitation. Those of skill in the art will readily recognize a variety of noncritical parameters that could be changed or modified to yield essentially similar results.

All publications, including sequences identified by accession number, and patent applications cited in this specification are herein incorporated by reference as if each individual publication or patent application were specifically and individually indicated to be incorporated by reference.

What is claimed is:

1. A method of enhancing expression of a transgene in a host cell, the method comprising introducing a replication adenovirus vector into a host cell, wherein the adenovirus vector comprises an endogenous adenovirus tripartite leader sequence and a hybrid expression cassette comprising a cytomegalovirus (CMV) immediate early promoter, a second adenovirus tripartite leader sequence, and the transgene; and expressing the transgene in the host cell.

2. The method of claim 1, wherein the adenovirus vector is selected from the group consisting of adenovirus type 2, adenovirus type 4, adenovirus type 5, and adenovirus type 7.

3. The method of claim 2, wherein the adenovirus vector is adenovirus type 2.

4. The method of claim 2, wherein the adenovirus vector is adenovirus type 4.

5. The method of claim 2, wherein the adenovirus vector is adenovirus type 5.

6. The method of claim 2, wherein the adenovirus vector is adenovirus type 7.

7. The method of claim 1, wherein the adenovirus vector lacks a functional E3 region.

8. The method of claim 7, wherein the vector is deleted in the E3 region.

9. The method of claim 7, wherein the transgene is an HIV gene.

10. The method of claim 9, wherein the HIV gene is an HIV regulatory gene.

11. The method of claim 10, wherein the HIV regulatory gene encodes Nef or Tat.

12. The method of claim 11, wherein the HIV regulatory gene encodes Nef.

13. The method of claim 12, wherein Nef is not myristoylated.

14. The method of claim 11, wherein the HIV regulatory gene encodes Tat.

15. The method of claim 14, wherein the Tat lacks transactivation function.

16. The method of claim 9, wherein the HIV gene is an HIV structural gene.

17. The method of claim 15, wherein the HIV structural gene encodes Gag or Env.

18. The method of claim 8, wherein the hybrid expression cassette is inserted into the deleted E3 region.

19. The method of claim 1, wherein the second adenovirus tripartite leader sequence is a spliced tripartite leader sequence.

20. The method of claim 1, wherein the second adenovirus tripartite leader sequence comprises the sequence of SEQ ID NO: 1.

21. The method claim 1, wherein the second adenovirus tripartite leader sequence comprises the sequence of SEQ ID NO: 2.

* * * * *